(12) United States Patent
Fowkes et al.

(10) Patent No.: US 7,092,749 B2
(45) Date of Patent: Aug. 15, 2006

(54) SYSTEM AND METHOD FOR ADAPTING THE BEHAVIOR OF A DIAGNOSTIC MEDICAL ULTRASOUND SYSTEM BASED ON ANATOMIC FEATURES PRESENT IN ULTRASOUND IMAGES

(75) Inventors: Kenneth M. Fowkes, Mountain View, CA (US); Lewis J. Thomas, III, Palo Alto, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 95 days.

(21) Appl. No.: 10/459,650

(22) Filed: Jun. 11, 2003

(65) Prior Publication Data

US 2004/0254439 A1    Dec. 16, 2004

(51) Int. Cl.
*A61B 8/00* (2006.01)

(52) U.S. Cl. ........................ 600/407; 600/443

(58) Field of Classification Search ........... 600/407, 600/443, 447, 409; 382/155–161, 128–131
See application file for complete search history.

(56) References Cited

U.S. PATENT DOCUMENTS

| | | | | |
|---|---|---|---|---|
| 5,239,591 A * | 8/1993 | Ranganath | .......... | 382/128 |
| 5,505,204 A | 4/1996 | Picot et al. | | |
| 5,538,003 A | 7/1996 | Gadonniex et al. | | |
| 5,709,210 A | 1/1998 | Green et al. | | |
| 5,800,356 A | 9/1998 | Criton et al. | | |
| 5,871,019 A * | 2/1999 | Belohlavek | .......... | 600/450 |
| 5,923,770 A * | 7/1999 | O'Donnell et al. | .......... | 382/131 |
| 6,106,466 A * | 8/2000 | Sheehan et al. | .......... | 600/443 |
| 6,149,594 A * | 11/2000 | Rock et al. | .......... | 600/437 |
| 6,176,830 B1 | 1/2001 | Freiburger | | |
| 6,295,464 B1 | 9/2001 | Metaxas | | |
| 6,322,509 B1 | 11/2001 | Pan et al. | | |
| 6,346,124 B1 * | 2/2002 | Geiser et al. | .......... | 600/450 |
| 6,390,984 B1 | 5/2002 | Pan et al. | | |
| 6,423,006 B1 | 7/2002 | Banjanin | | |
| 6,425,865 B1 * | 7/2002 | Salcudean et al. | .......... | 600/437 |
| 6,463,167 B1 * | 10/2002 | Feldman et al. | .......... | 382/128 |
| 6,464,640 B1 | 10/2002 | Guracar et al. | | |
| 6,464,641 B1 | 10/2002 | Pan et al. | | |
| 6,612,988 B1 * | 9/2003 | Maor et al. | .......... | 600/439 |
| 6,716,175 B1 * | 4/2004 | Geiser et al. | .......... | 600/450 |
| 6,793,496 B1 * | 9/2004 | Edic et al. | .......... | 434/262 |
| 6,816,607 B1 * | 11/2004 | O'Donnell et al. | .......... | 382/131 |

* cited by examiner

*Primary Examiner*—Francis J. Jaworski

(57) ABSTRACT

A diagnostic medical imaging system is disclosed, such as a diagnostic medical ultrasound system, which uses operational rules or an anatomic model of an anatomical structure as an organizational framework for applying anatomy-specific auxiliary/secondary information. After processing the operational rules on the acquired images or associating the model with the acquired images, adapting/fitting the model to match the images if necessary, the imaging system can associate aspects of the images being acquired with the auxiliary/secondary information, allowing the imaging system to behave as if it "knows" what it is scanning. The auxiliary information may be rules that affect the behavior of the imaging system, or may be the acquired image samples. System behavior may then be automatically adapted or the operator may be prompted to make operational changes.

50 Claims, 25 Drawing Sheets

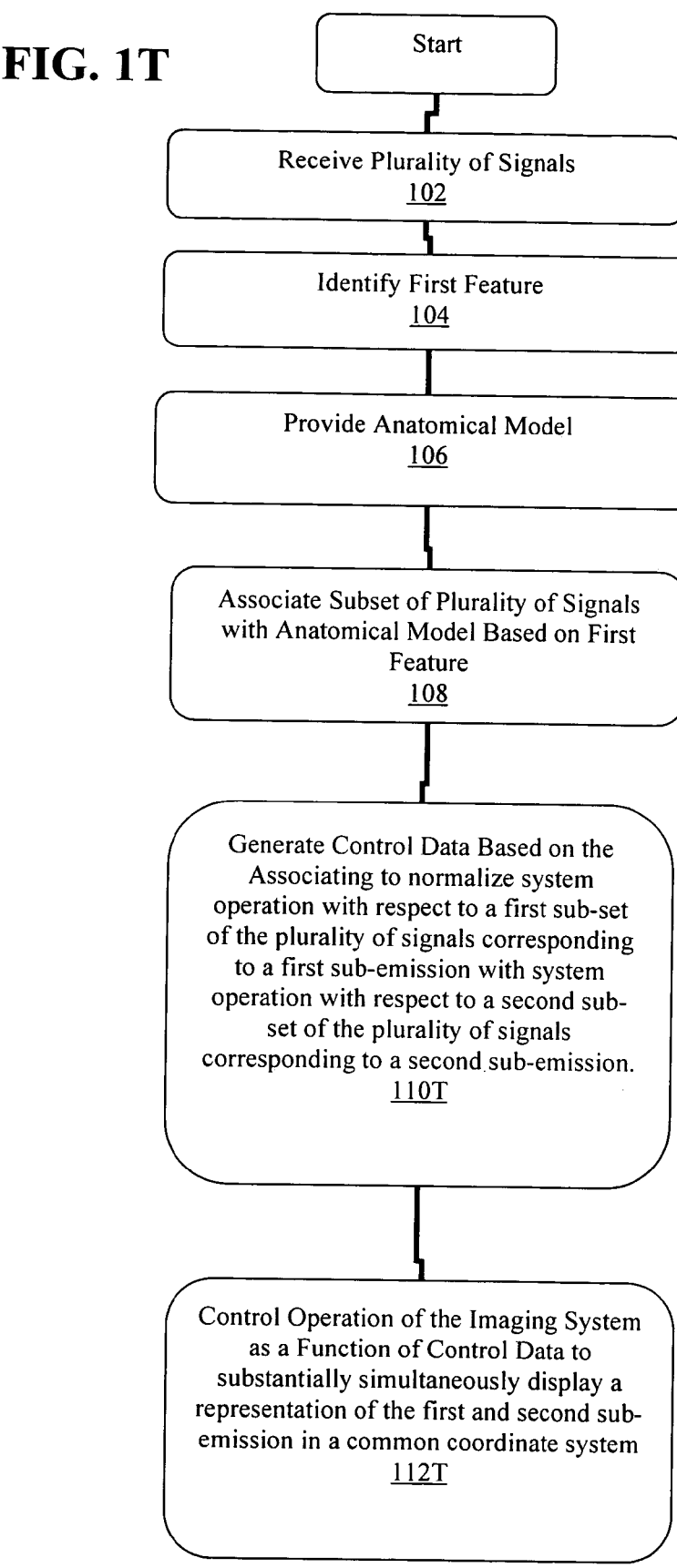

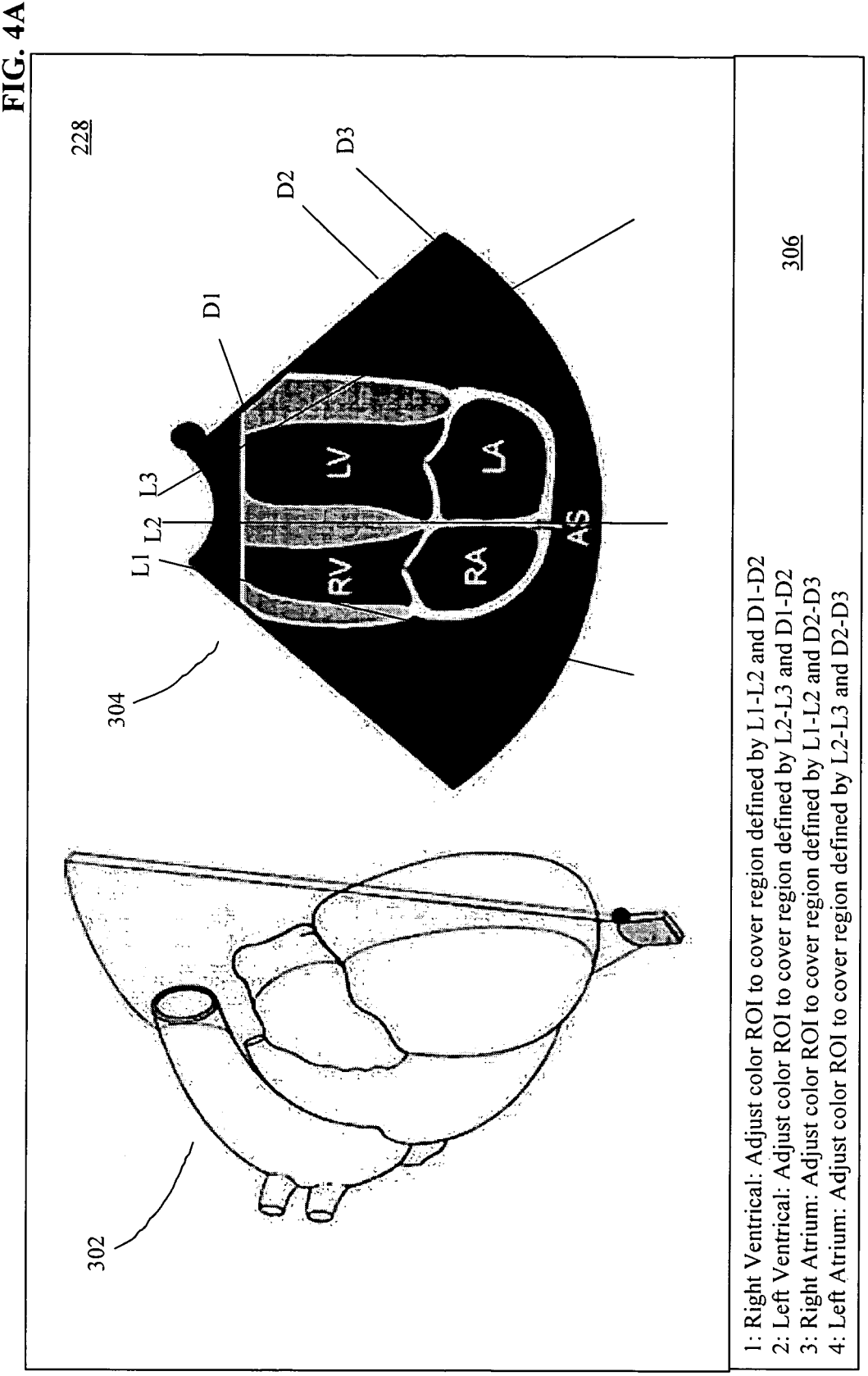

SYSTEM AND METHOD FOR ADAPTING THE BEHAVIOR OF A DIAGNOSTIC MEDICAL ULTRASOUND SYSTEM BASED ON ANATOMIC FEATURES PRESENT IN ULTRASOUND IMAGES

BACKGROUND

Imaging systems, such as diagnostic medical ultrasound systems, are routinely used in medical applications for the purpose of imaging various body tissues and organs and for other diagnostic and therapeutic purposes. These systems allow medical professionals to view the internal conditions of a patient thereby enabling them to render a better diagnosis. In one example of a diagnostic medical ultrasound system, a piezoelectric transducer acquires image data by transmitting a series of ultrasonic pulses into a patient and receiving the reflected echoes therefrom. These echoes are converted/manipulated into an image and displayed on a monitor or stored for later use.

Imaging systems are generally active devices, i.e. relying on transmitting some form of energy, such as acoustic waves or x-rays, into a subject and detecting emissions from, or absorption by, the subject in response to that energy. Passive medical diagnostic systems, in contrast, rely solely on detecting the natural emissions from a subject, such as acoustic, electrical, magnetic or thermal emissions. Exemplary passive systems include electrocardiogram devices or thermal imaging devices. Active systems may be combined with passive systems, such as a diagnostic medical ultrasound system which features an electrocardiogram detector.

At the most basic level, current imaging systems, whether active, passive or combinations thereof, are only capable of determining the presence, including relative location, intensity and duration, or absence of a detectable emission within their field of view and reporting that determination in some manner to the user. For example, a diagnostic medical ultrasound system is capable of detecting all acoustic-reflective tissues within the transducer's field of view by detecting the reflected echoes, as described above. The ultrasound system computes the location, intensity and duration of the detected responses and plots/renders them on a two dimensional display for the user. This has the effect of creating an acoustic image of the portion of the subject being scanned.

Unfortunately, current imaging systems are incapable of identifying or "knowing" what they are imaging. A trained imaging technician is still required to interpret the images, determine what is being imaged and render a diagnosis. Further, depending on the portion of the subject being imaged, adjustments to the imaging system may be necessary to achieve optimal viewing, and therefore optimal diagnosis. Such adjustments, such as beam angle or beam focus in the case of ultrasound, must also be made by a trained imaging technician who recognizes the anatomical structures being imaged and is cognizant of the adjustments necessary to achieve an optimal image.

Some imaging systems permit the operator to identify the anatomical structure being imaged to the imaging system. Once identified, the imaging system then makes automatic adjustments to particular imaging parameters based on information with which it has been programmed in regard to the operator-identified structure. Unfortunately, this requires that the operator make an accurate determination as to the anatomical structures being imaged, as well as select the proper imaging mode to which the automatically adjusted imaging parameters apply, and that the structures conform substantially to the system programming. Such manual identification, however, creates a distraction from the examination process. Further, if the structure being imaged is diseased or otherwise fails to conform to the programming of the imaging system, the imaging system may make incorrect adjustments resulting in sub-optimal imaging. In addition, such manual identification and accompanying adjustments are static and cannot account for certain anatomical structures which are dynamic in nature.

Accordingly, there is a need for a diagnostic medical imaging system which is capable of comprehending the anatomical structures being imaged so as to optimize the imaging of, and/or perform functions, on the image of those structures.

SUMMARY

The present invention is defined by the following claims, and nothing in this section should be taken as a limitation on those claims. By way of introduction, the preferred embodiments described below relate to a diagnostic medical imaging system. The system includes a receiver operative to receive a plurality of signals, each of the plurality of signals having been derived from an emission detected by the diagnostic medical imaging system from a portion of a subject, the portion characterized by a first feature comprehensible by the diagnostic medical imaging system from at least one of the plurality of signals and a second feature at least partially incomprehensible by the diagnostic medical imaging system from the plurality of signals, the first and second features comprising first and second features of at least one anatomical structure at least partially present in the portion. In addition the system includes a processor coupled with the receiver and operative receive the plurality of signals from the receiver and to identify the first feature. Further, the system includes a memory coupled with the processor and operative to store an anatomical model, the anatomical model comprising a substantial approximation of the second feature of the at least one anatomical structure, the anatomical model being comprehensible by the diagnostic medical imaging system and defining at least one expected characteristic of the second feature. Wherein the processor is further operative to associate a subset of the plurality of signals with the anatomical model based on the first feature, generate control data based on the association, and control operation of the diagnostic medical imaging system as a function of the control data.

The preferred embodiments further relate to a method for controlling the operation of a diagnostic medical imaging system. In one embodiment, the method includes: receiving a plurality of signals, each of the plurality of signals having been derived from an emission detected by the diagnostic medical imaging system from a portion of a subject, the portion characterized by a first feature comprehensible by the diagnostic medical imaging system from at least one of the plurality of signals and a second feature at least partially incomprehensible by the diagnostic medical imaging system from the plurality of signals, the first and second features comprising first and second features of at least one anatomical structure at least partially present in the portion; identifying the first feature by the diagnostic medical imaging system; providing an anatomical model, the anatomical model comprising a substantial approximation of the second feature of the at least one anatomical structure, the anatomical model being comprehensible by the diagnostic medical imaging system and defining at least one expected characteristic of the second feature; associating a subset of the plurality of signals with the anatomical model based on the first feature; generating control data based on the associating; and controlling operation of the diagnostic medical imaging system as a function of the control data.

Further aspects and advantages of the invention are discussed below in conjunction with the preferred embodiments.

BRIEF DESCRIPTION OF THE DRAWINGS

FIG. 4A depicts an exemplary anatomical model of the heart.

DETAILED DESCRIPTION OF THE DRAWINGS AND PRESENTLY PREFERRED EMBODIMENTS

Figure 1A:
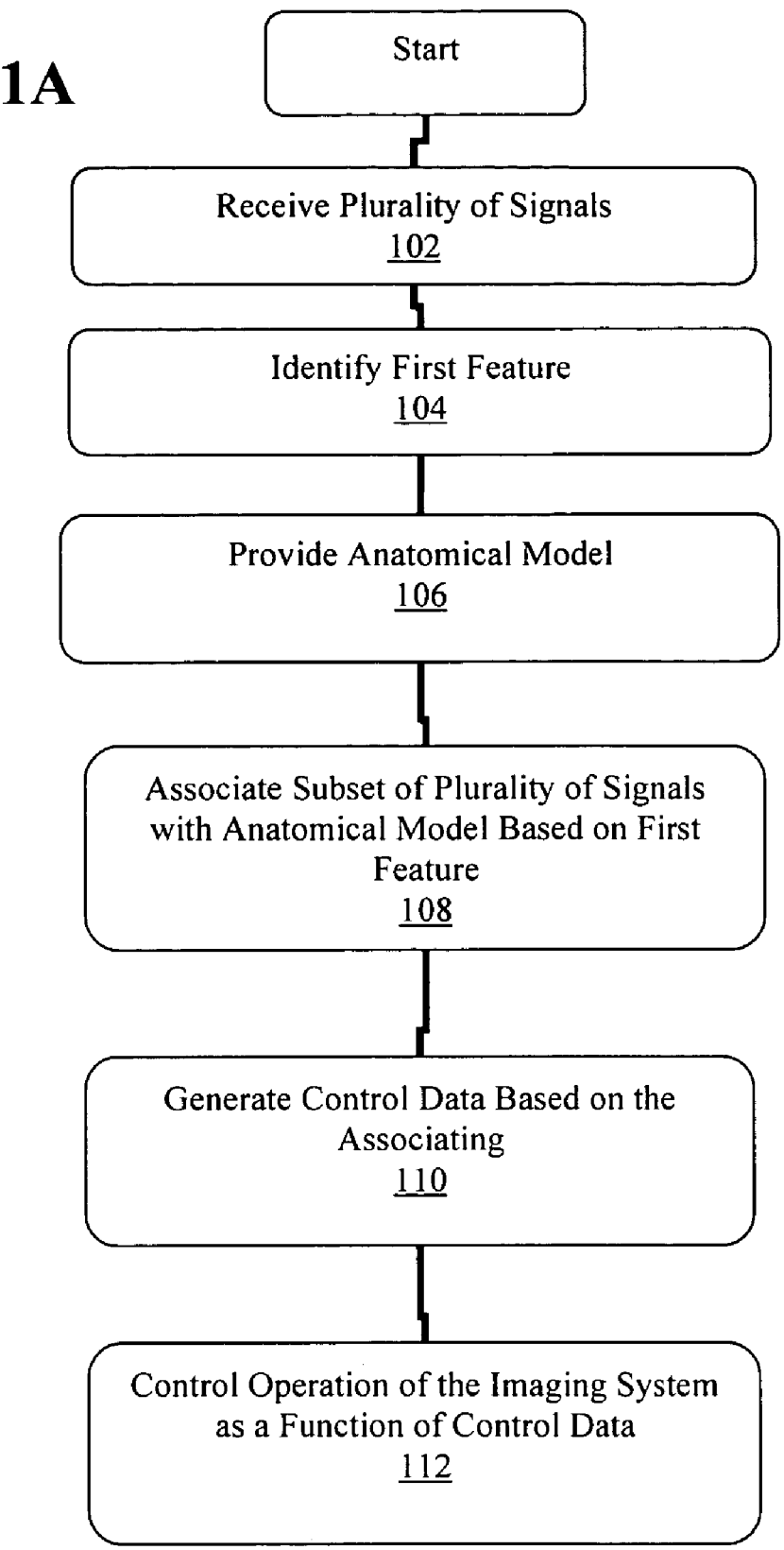
FIGS. 1A–1T depict flow charts of the operation of an imaging system, according to one embodiment.
Figure 1B:
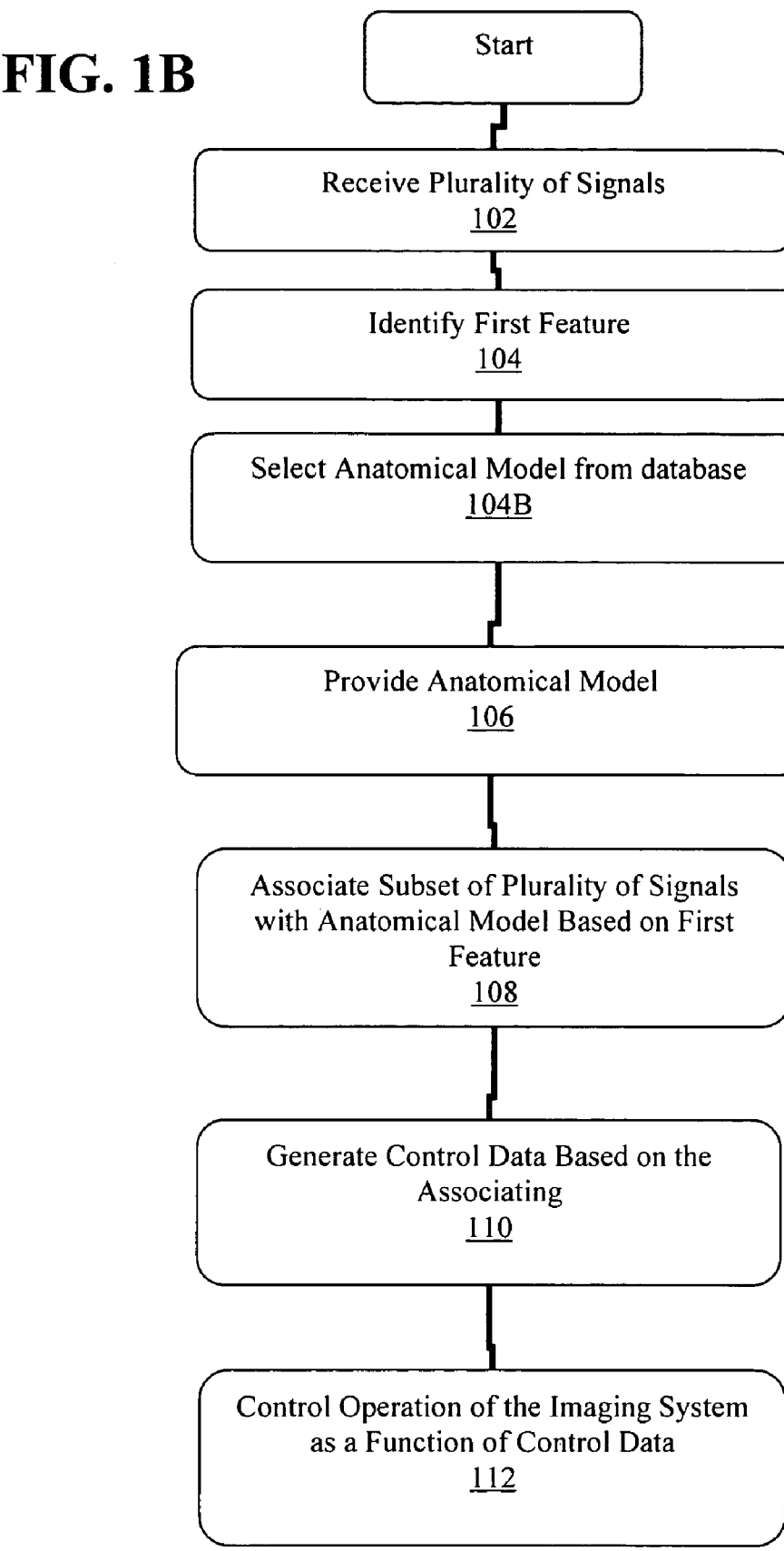
Figure 1C:
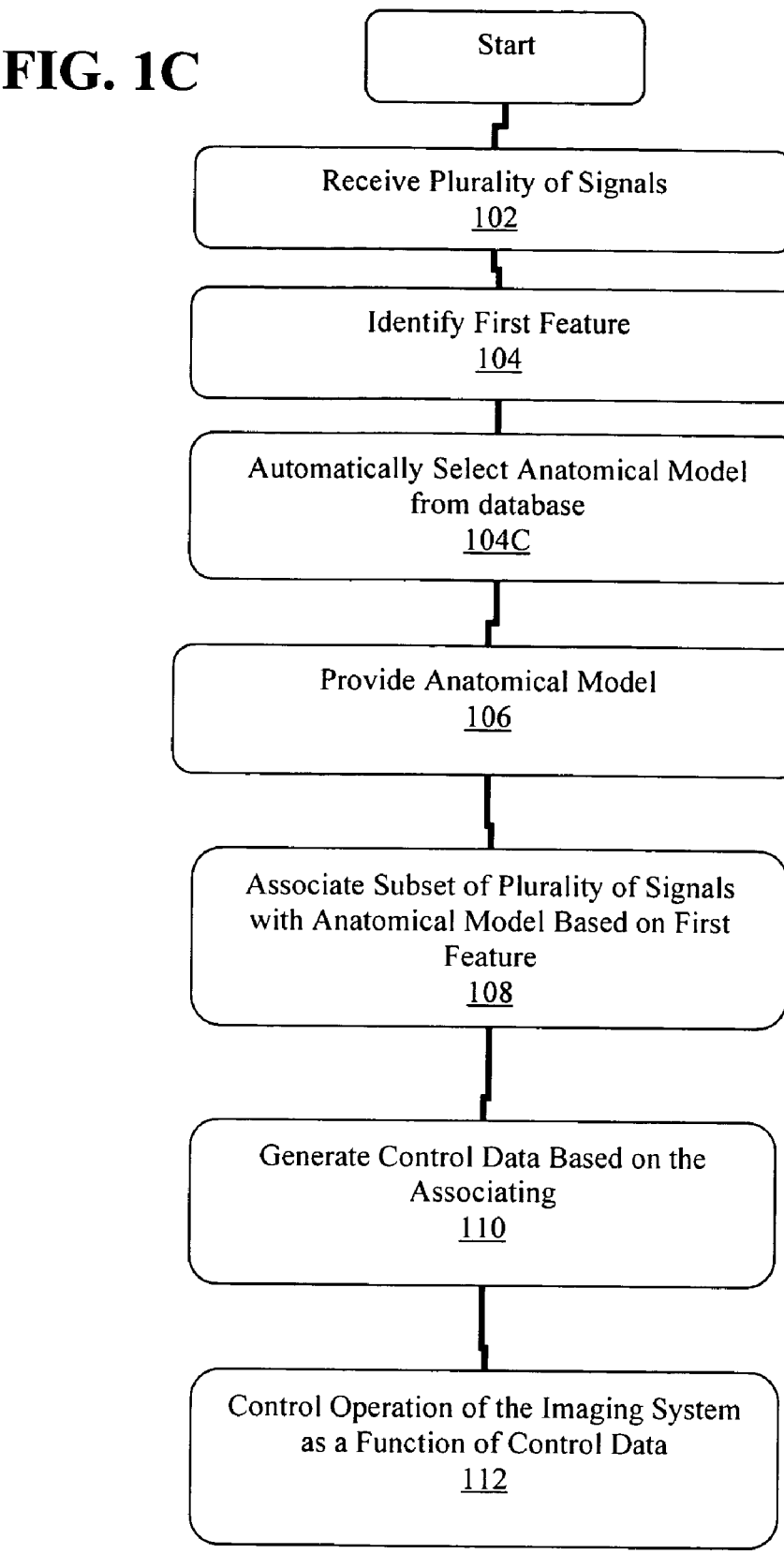
Figure 1D:
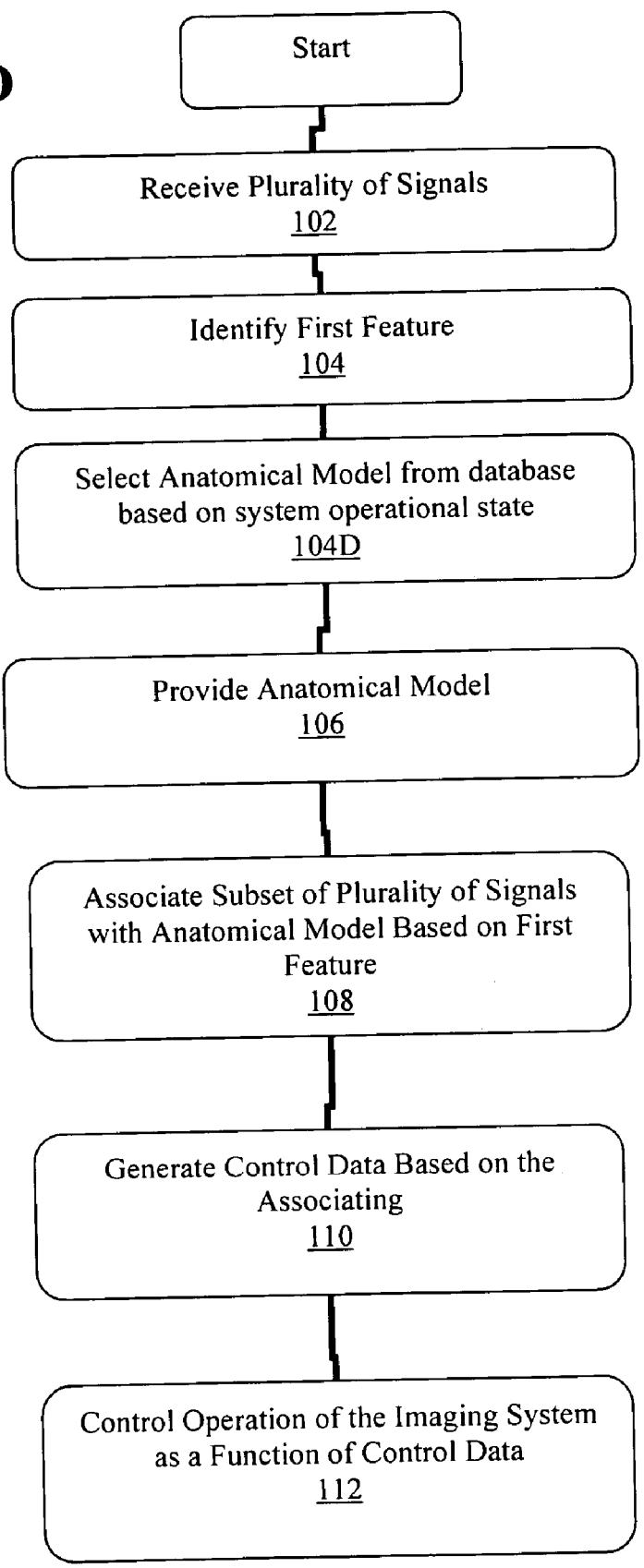
Figure 1E:
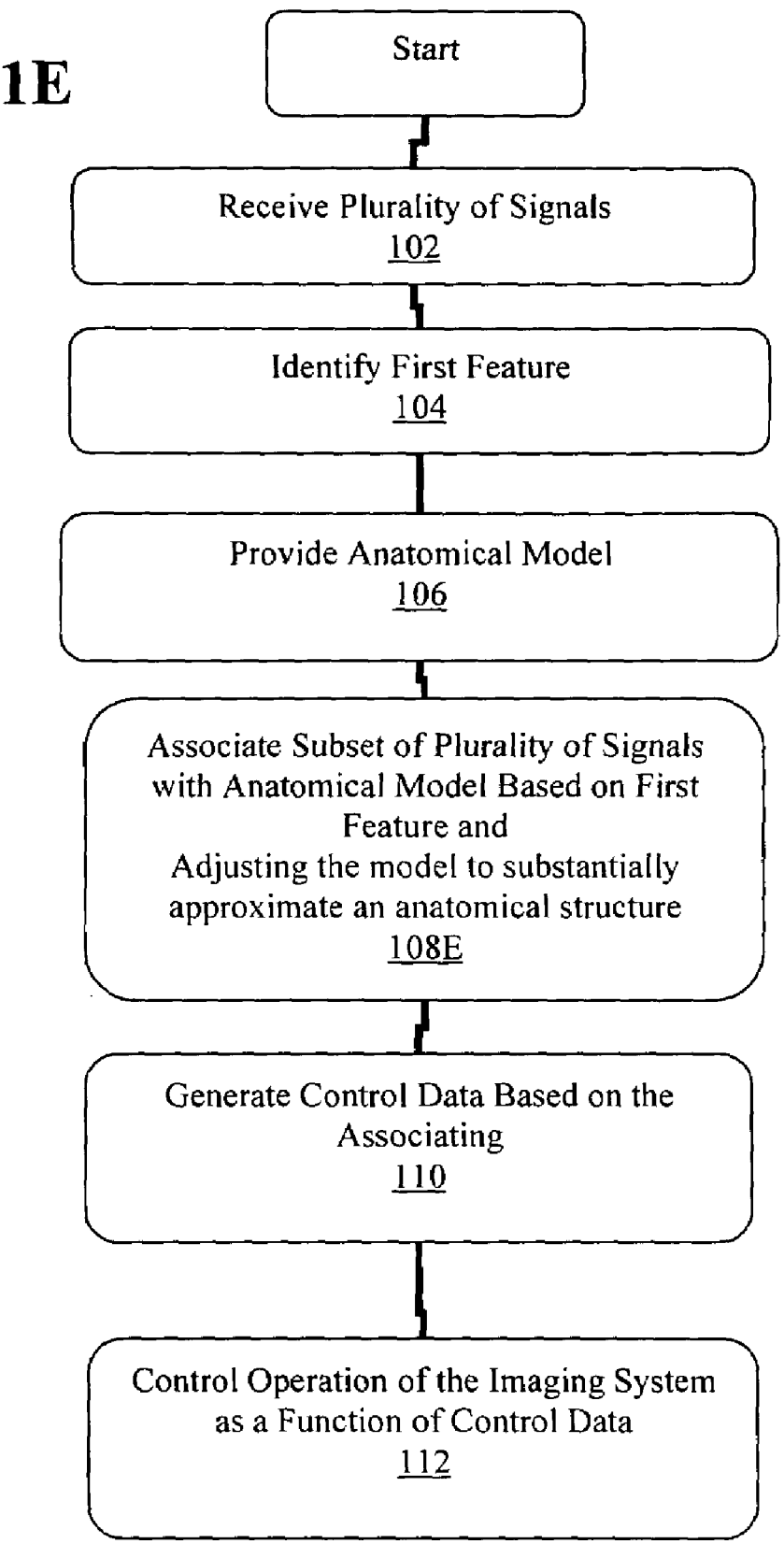
Figure 1F:
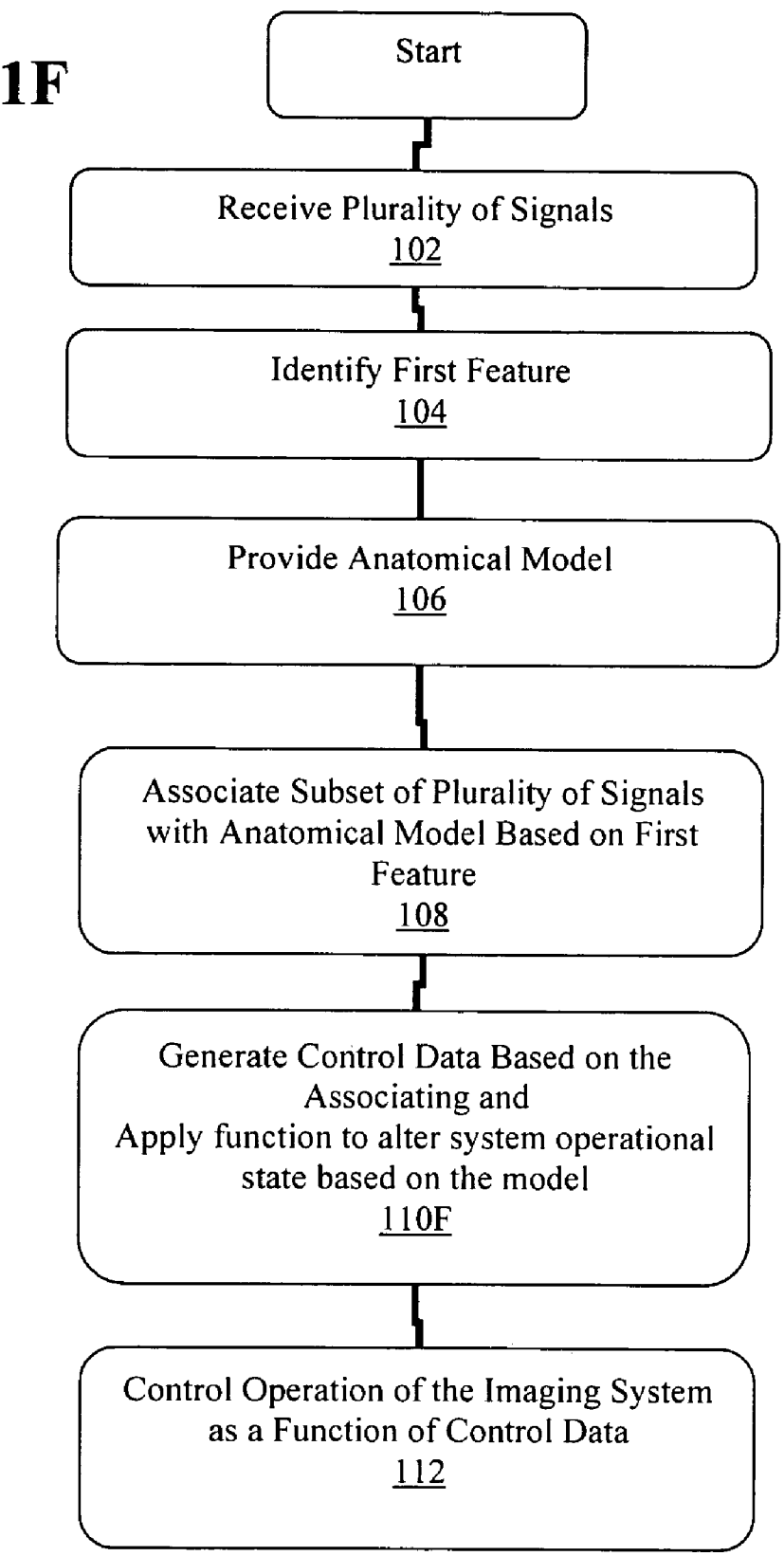
Figure 1G:
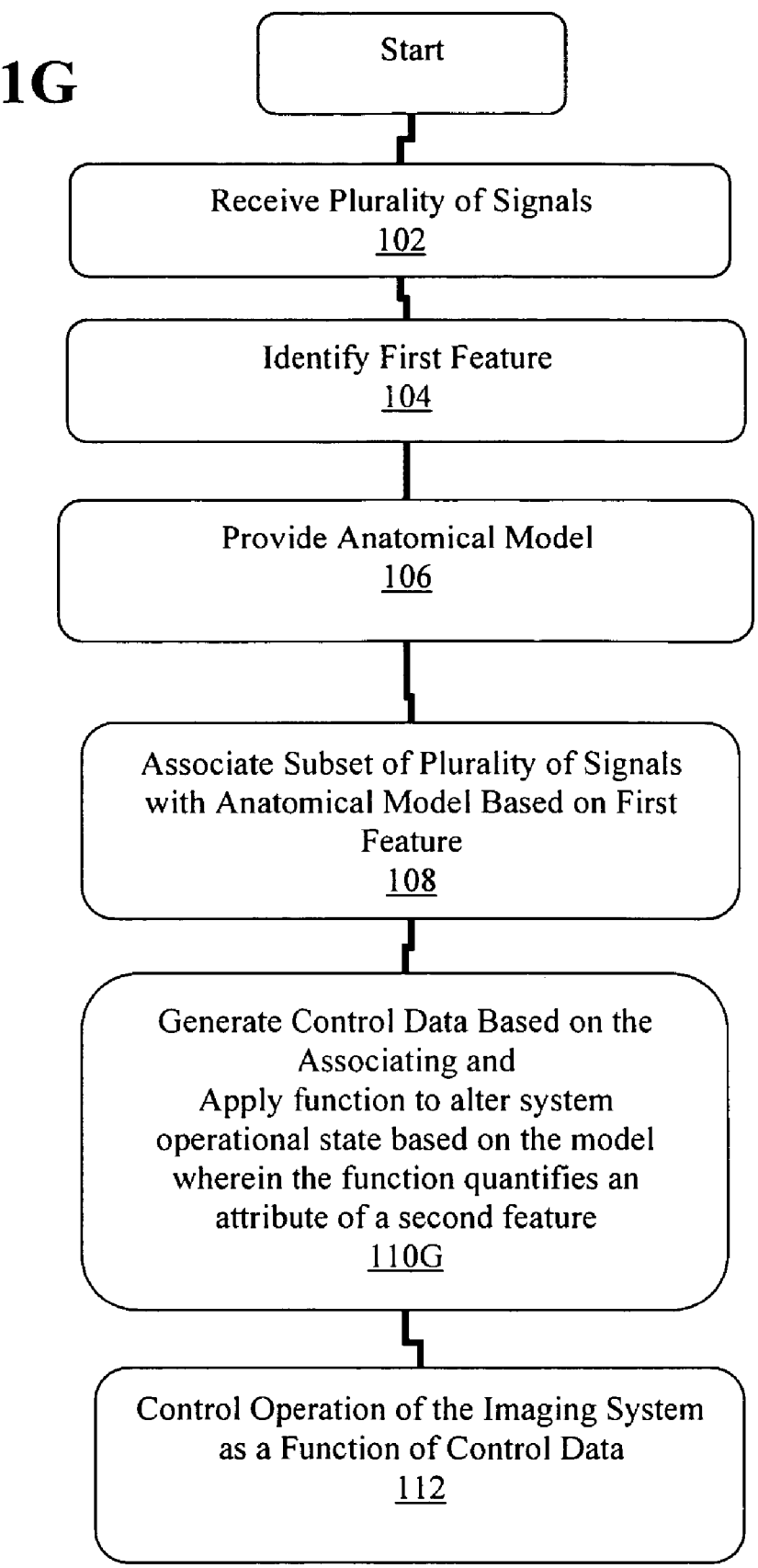
Figure 1H:
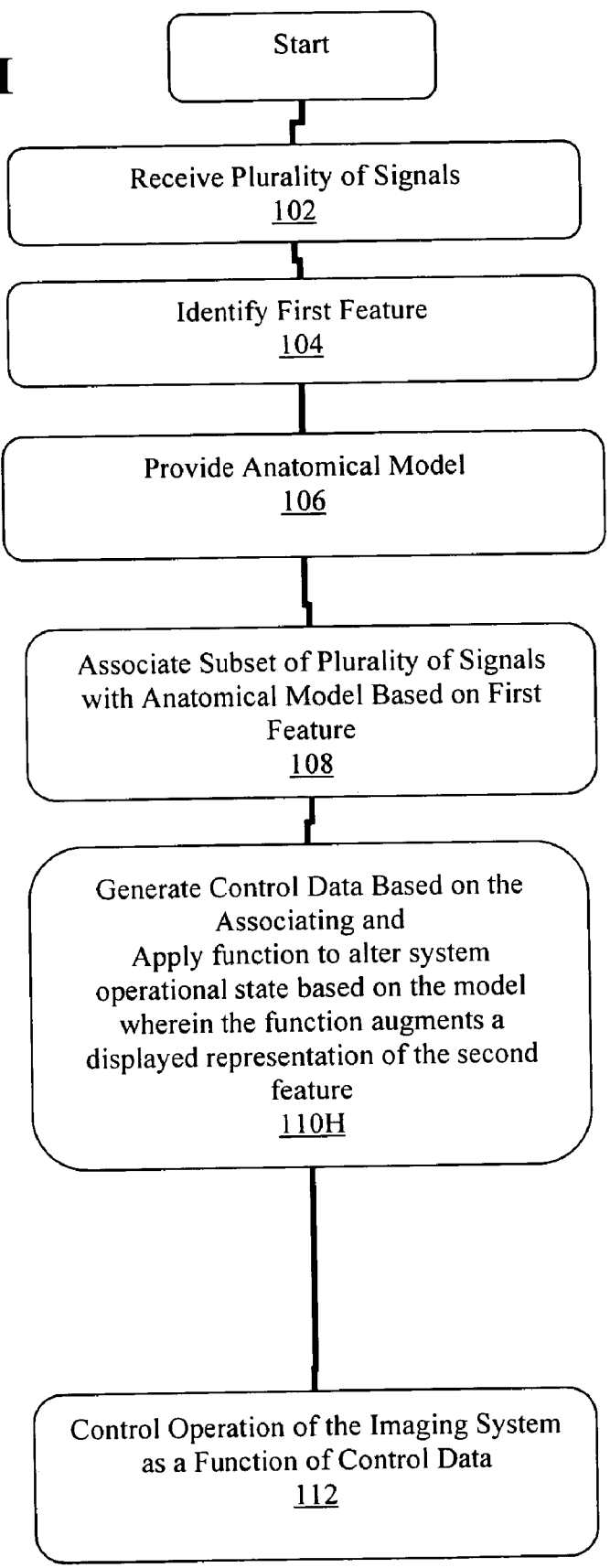
Figure 1I:
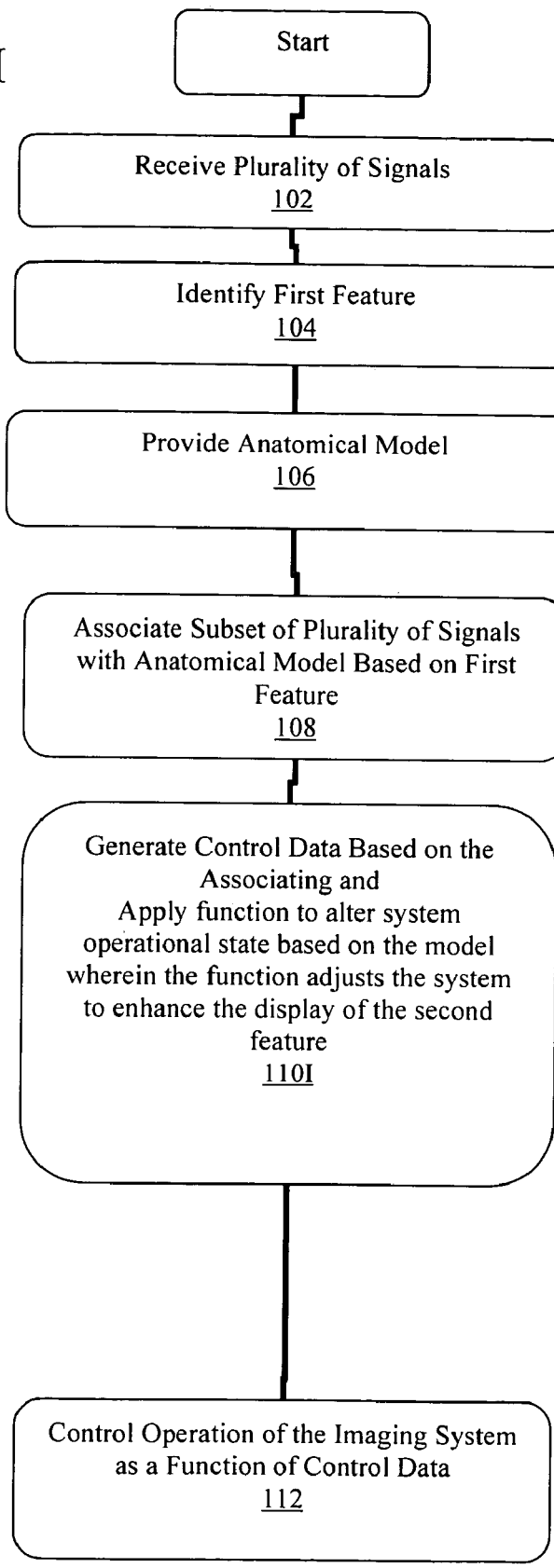
Figure 1J:
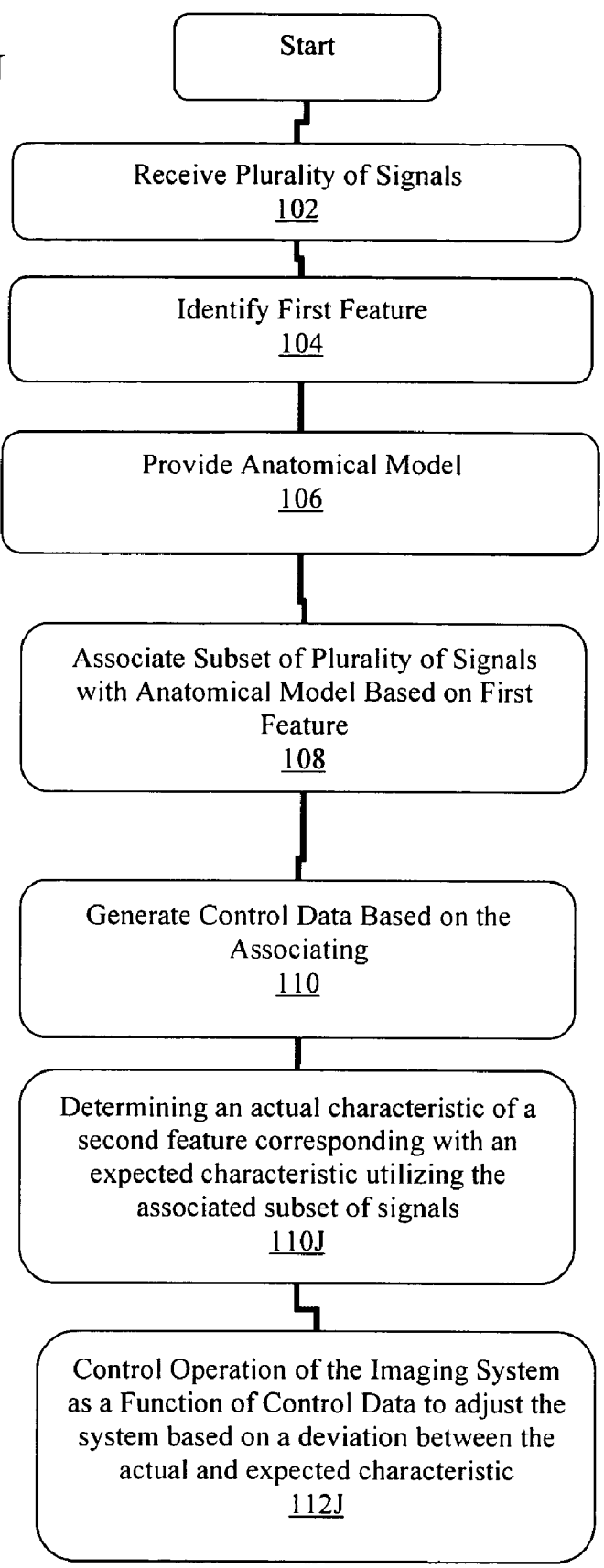
Figure 1K:
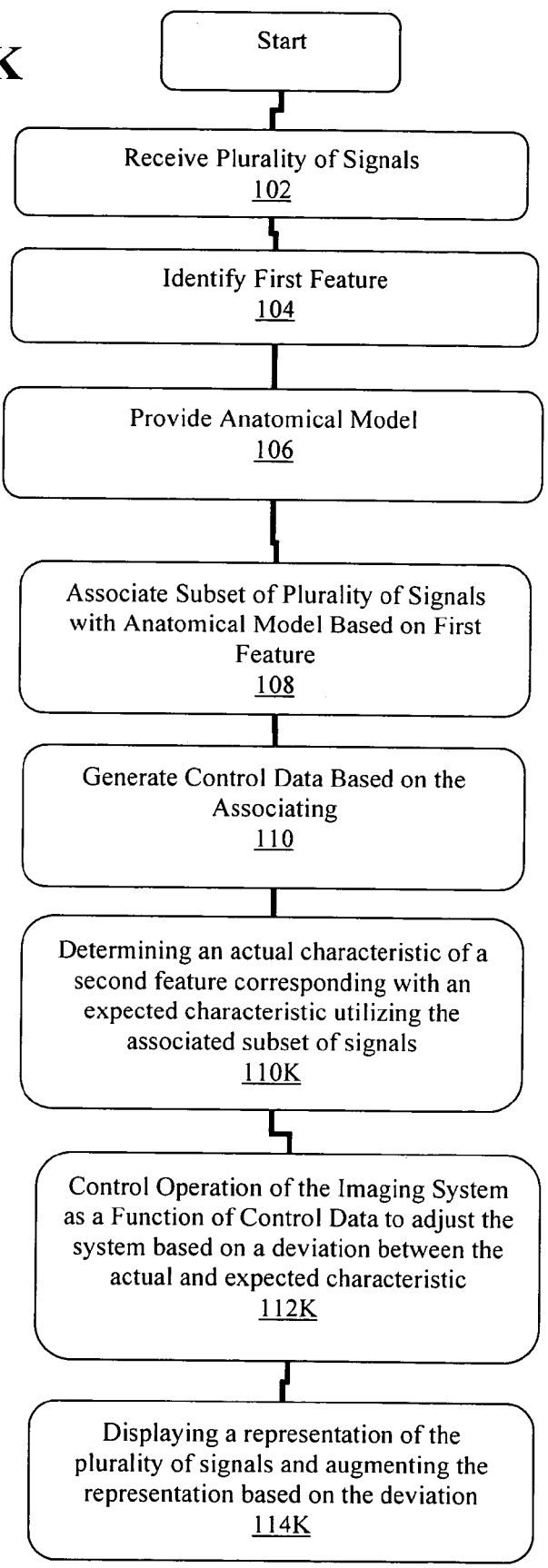
Figure 1L:
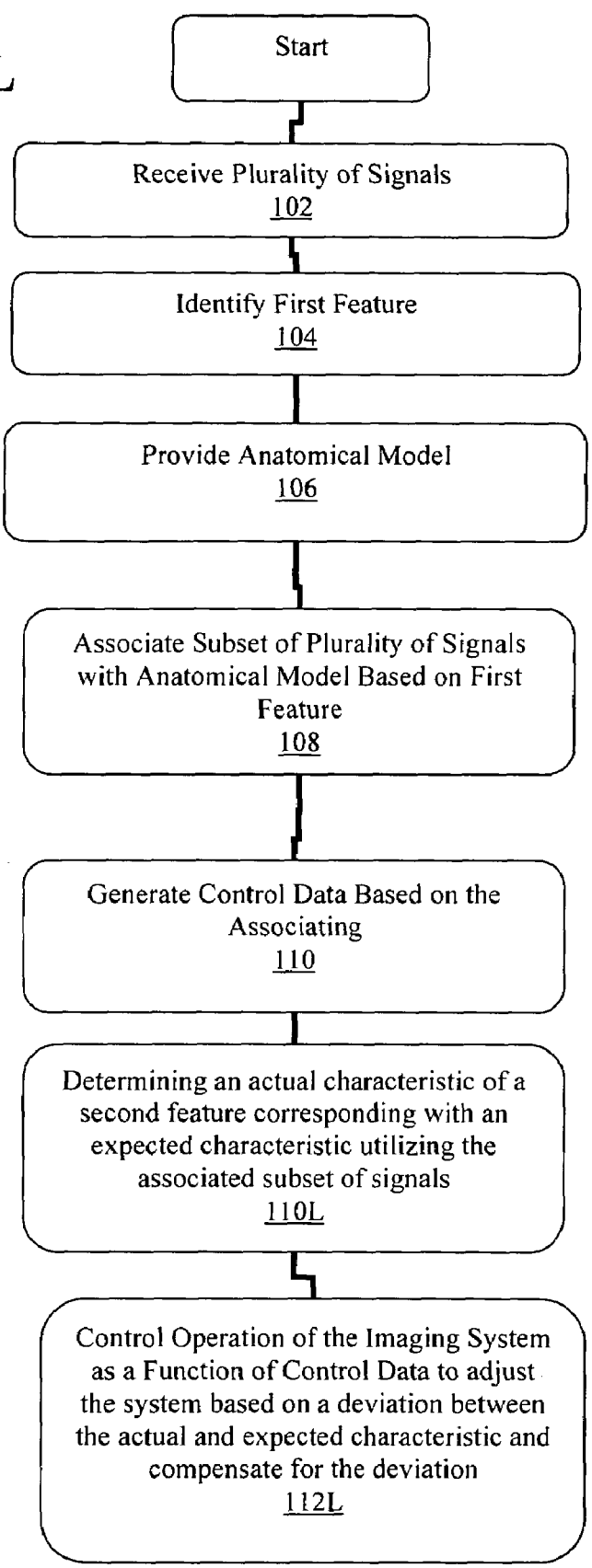
Figure 1M:
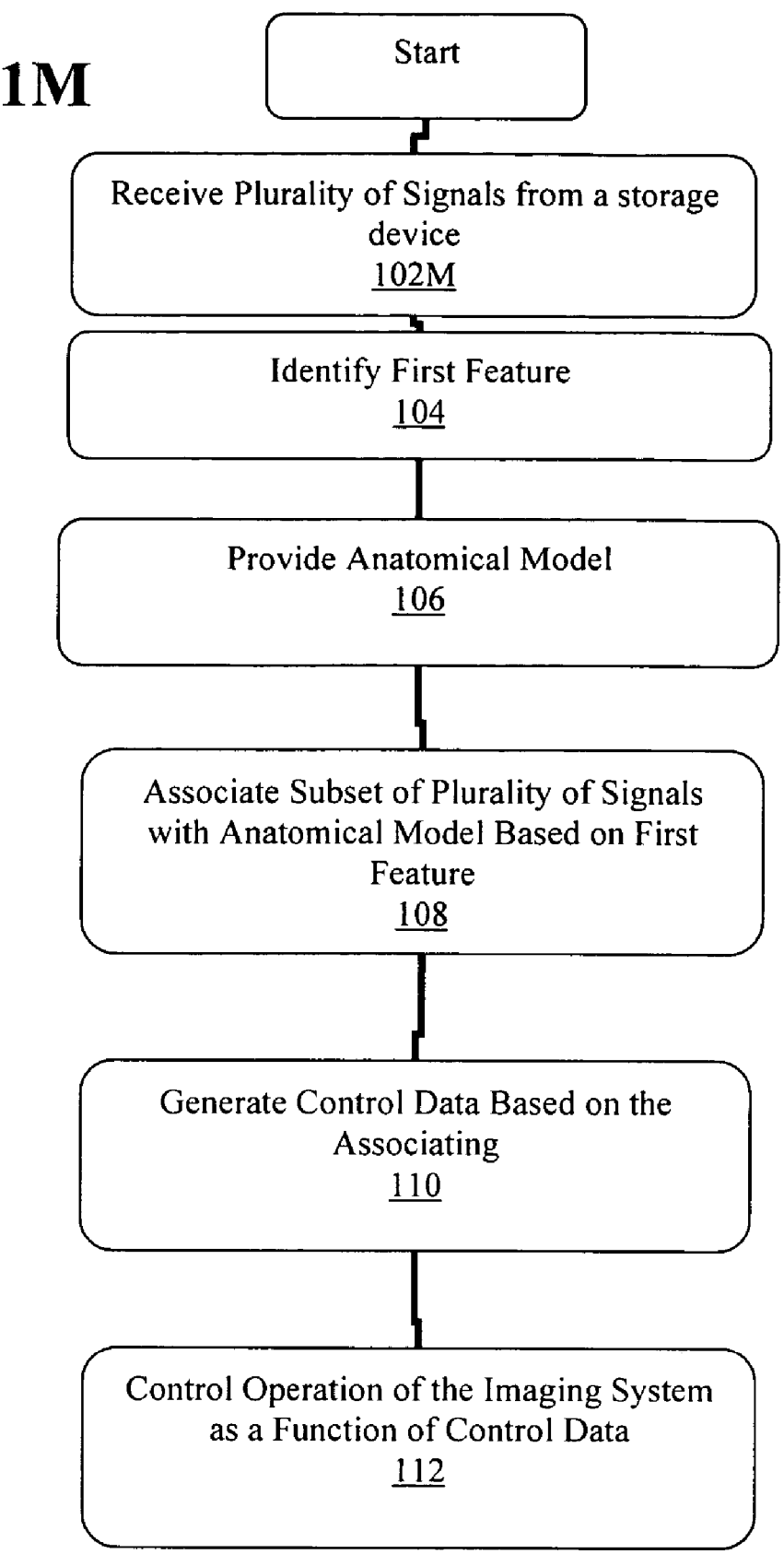
Figure 1N:
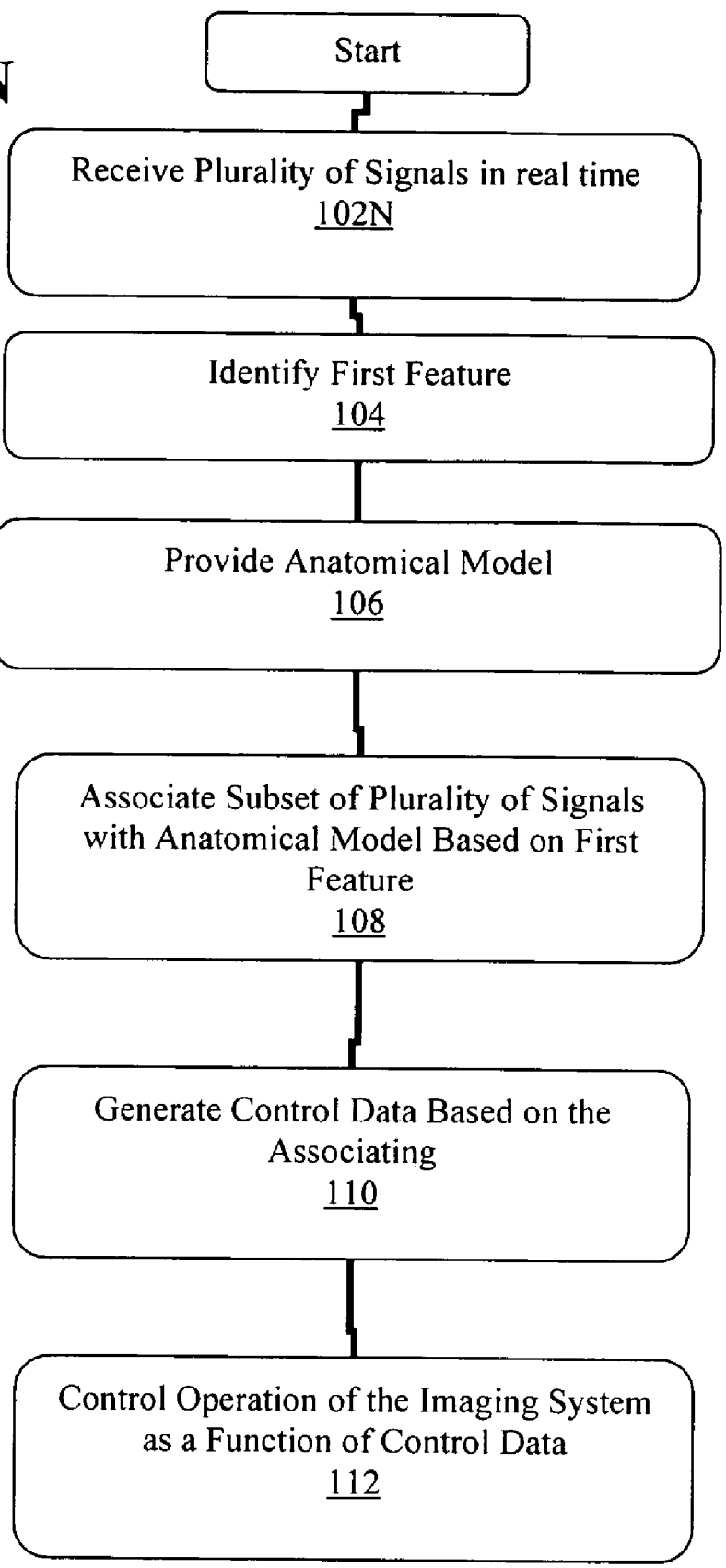
Figure 10:
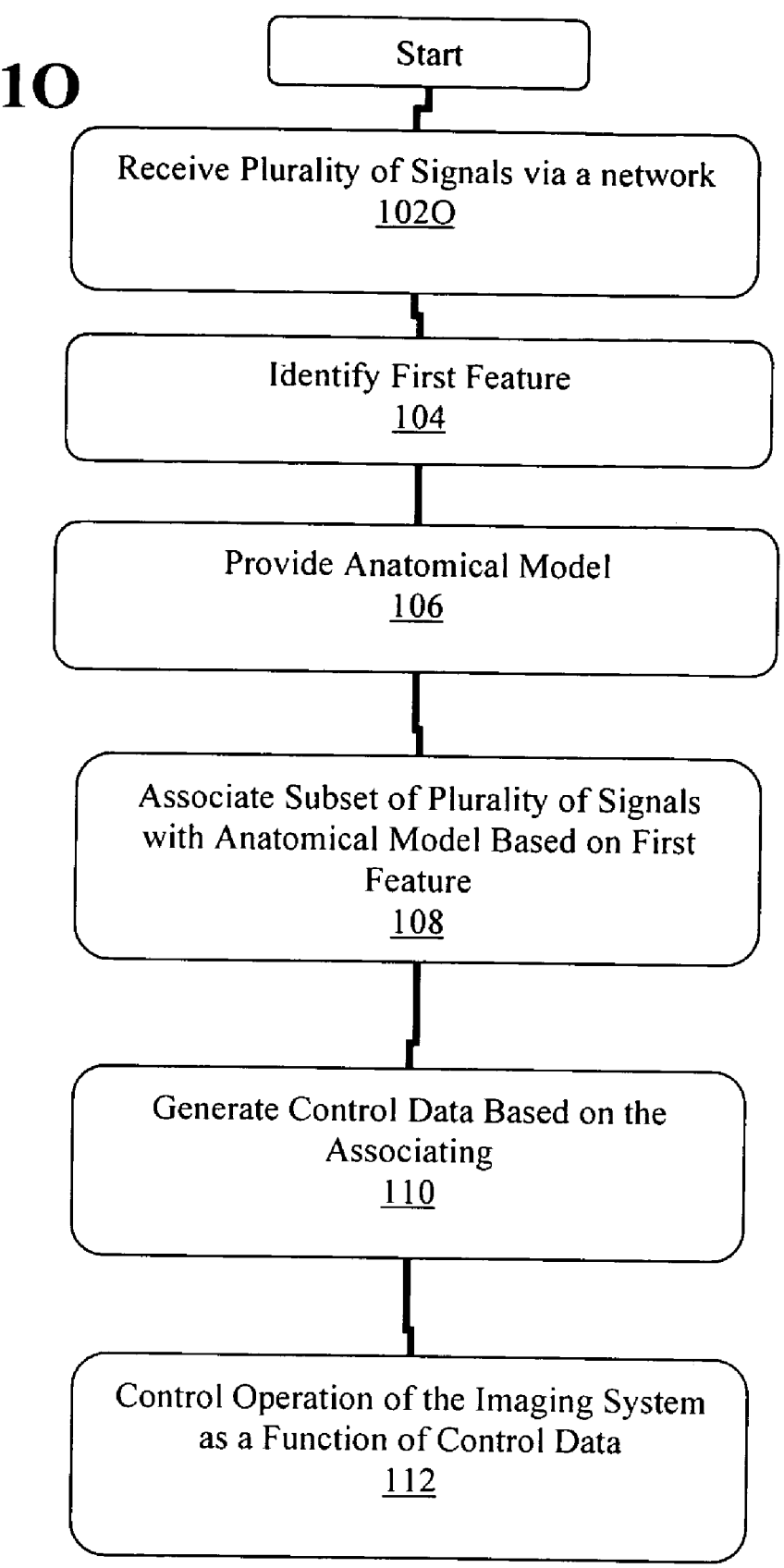
Figure 1P:
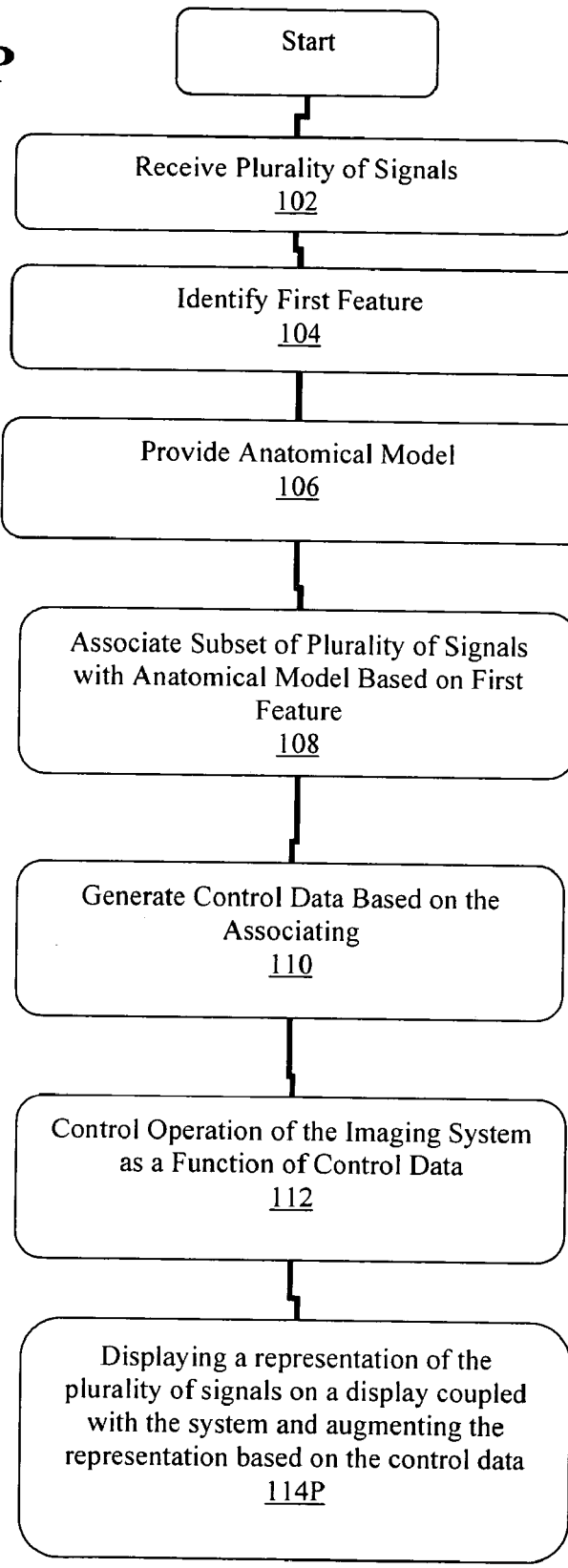
Figure 1Q:
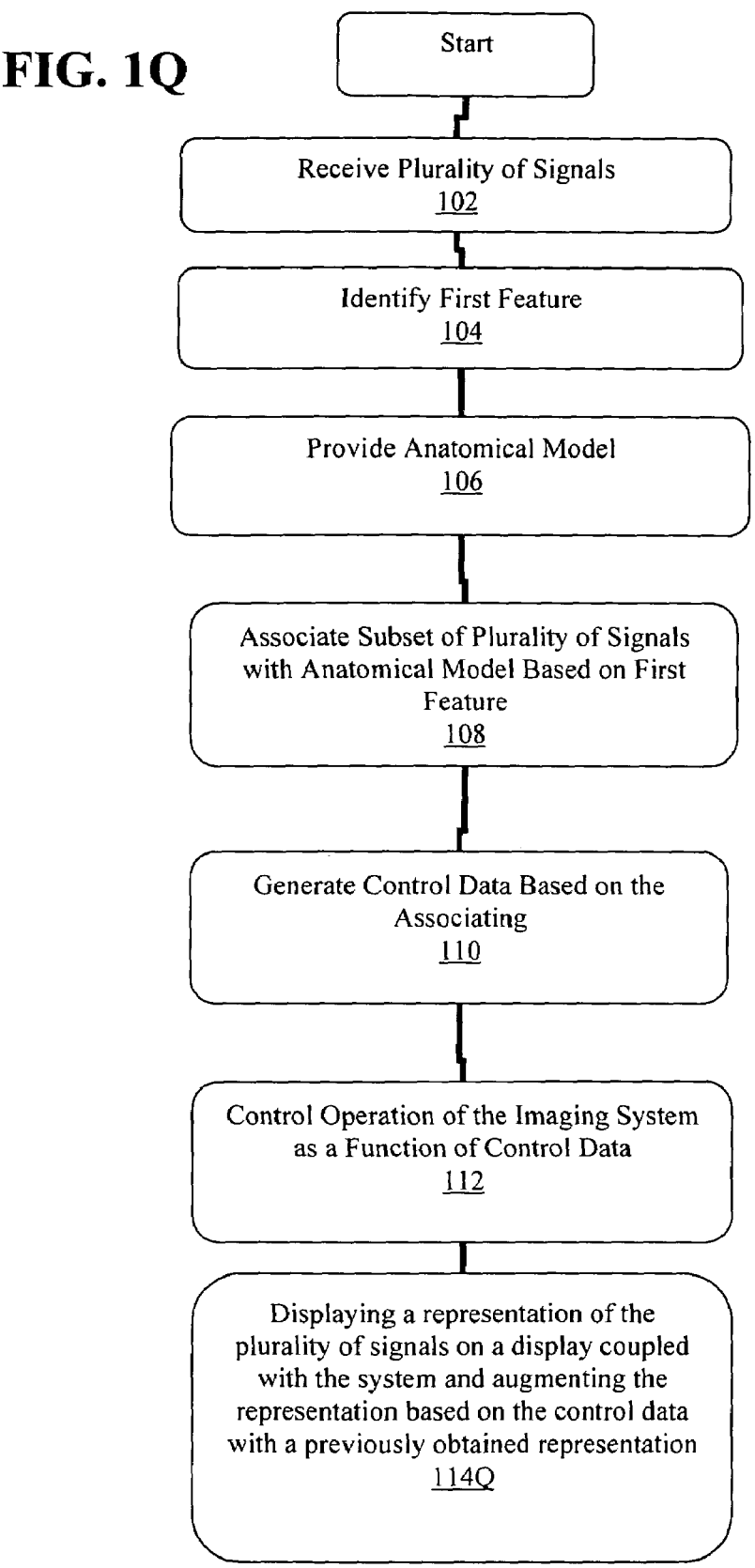
Figure 1R:
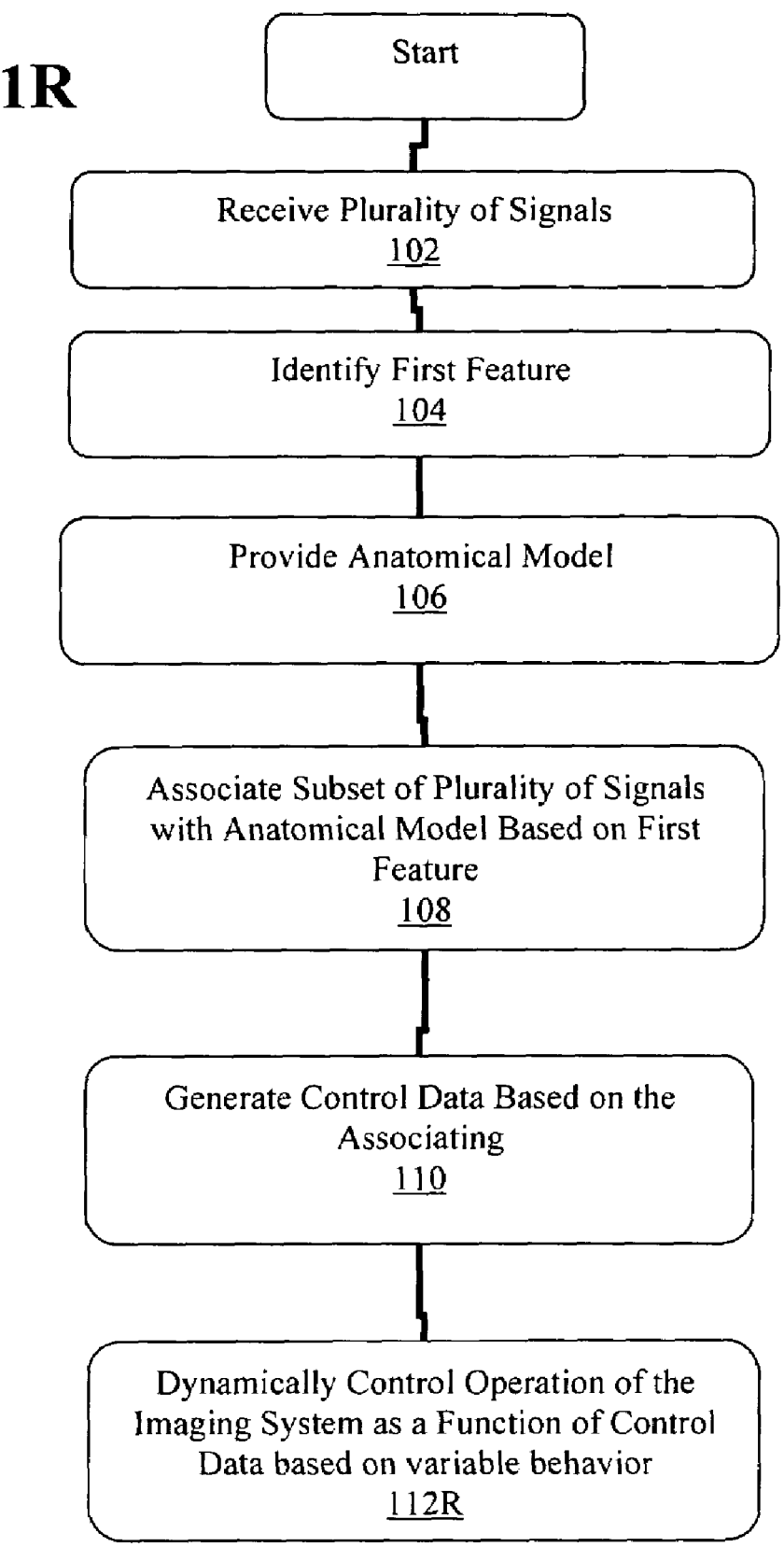
Figure 1S:
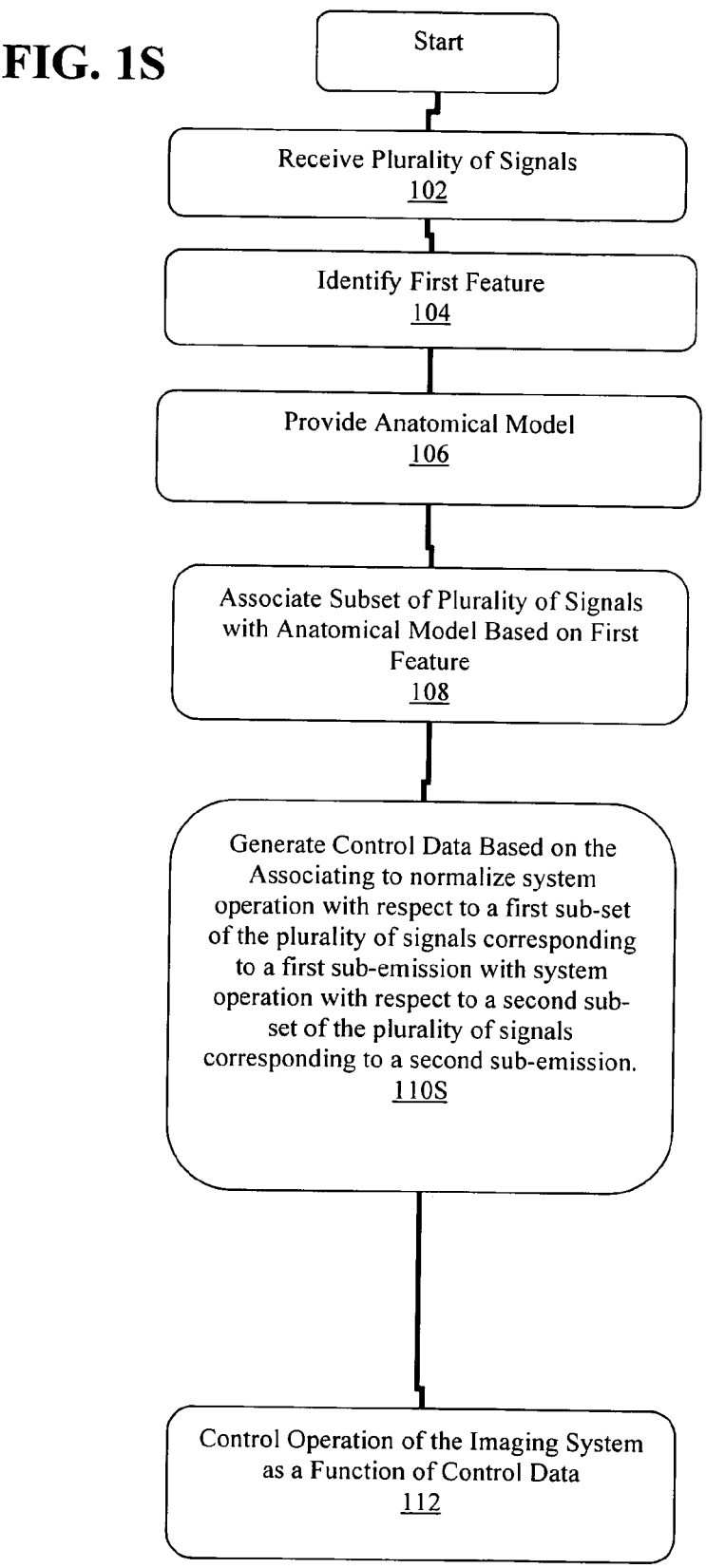

The disclosed embodiments relate to an imaging system, such as a diagnostic medical ultrasound system, which uses an operational rule set or volumetric computer model of an anatomical structure as an organizational framework for applying anatomy-specific auxiliary/secondary information. After adapting/fitting the model to match the images being acquired, if necessary, the imaging system can associate aspects of the images being acquired with the auxiliary/secondary information, allowing the imaging system to behave as if it "knows" what it is scanning. The auxiliary information may be rules that affect the behavior of the imaging system, or may be the acquired image samples. Such imaging systems provide improved workflow for the operator, improving efficiency and diagnostic accuracy, by providing improved automation and improved operator/imaging system interfacing.

While the disclosed embodiments will be described in relation to diagnostic medical ultrasound systems, it will be appreciated that other diagnostic medical imaging systems are also contemplated, such as x-ray, computed tomography ("CT"), magnetic resonance imaging ("MRI"), etc. Further, both active and passive systems, as well as combinations thereof, are contemplated as well. For example, an electrocardiograph or thermal imaging system may also be used.

Some current diagnostic medical ultrasound systems automatically adjust acquisition and particular imaging parameters of the current imaging mode based on the operator's indication of the anatomical structures presently being scanned. Unfortunately, these indications by the operator are manual and static, i.e. once input, the settings remain fixed until they are changed by the operator, resulting in the acquisition and display parameters of the system remaining static. These systems are incapable of automatically determining the anatomical structures which may be present in the scan, dynamically varying the system control based on the different parts of a particular anatomical structure or varying the system control to account for different phases of a cyclically moving structure.

Further, some current imaging systems provide the capability to combine/stitch multiple images together to produce an image with an apparently larger field of view or to form a three-dimensional image. However, these capabilities are restricted to combining images that were acquired sequentially or utilizing extremely accurate position sensing devices to give the system enough information to properly assemble the images.

In addition, some current imaging systems require the operator to manually identify regions of interest ("ROI") within imaged portions in order to perform special functions on those regions, such as measuring fluid flow rates or applying a Doppler function. The system, however, is incapable of determining, itself, where to locate the ROI to perform these functions or maintaining the ROI alignment as the field of view shifts or otherwise changes, such as due to operator or patient movement.

The disclosed embodiments relate to an imaging system which utilizes an operational rule set or an anatomical model, volumetric and/or dynamic, as a framework to comprehend anatomical features not otherwise comprehensible by the system. This framework is associated with the actual anatomy based on those features of the subject that the system can comprehend. This association of the model with the actual anatomy being imaged may include fitting or otherwise adapting the model to more substantially approximate the actual anatomy, such as by adjusting the dimensions or the behavior. The model further includes secondary or auxiliary functions or data which, while not necessarily part of the model, are related to, or may be derived from, the model. These functions may include functions that the system would not be otherwise capable of performing without operator input. The association of the model with the actual anatomy forms derived associations between these secondary/auxiliary functions/data and the actual anatomy. Once associated, the system is capable of performing these functions or adapting operations with respect to the actual anatomy without manual input from the operator, or, alternatively, guiding/prompting the operator through manual performance of the functions or adapting operations. For example, systems settings and imaging parameters may be automatically set and/or dynamically varied to maintain optimal imaging as different portions of the subject are scanned. Further, images acquired during discrete scan sessions may be stitched together by utilizing the model as a guide. In addition, secondary information associated with the model may used to indicate to the system as to where to place ROI's for particular functions, e.g. a blood vessel model may include secondary information to cause the system to place an ROI for Doppler imaging between the vessel walls and maintain the position of the ROI as the scan progresses.

It is known to map acquired images of a particular anatomical structure to a computer model of that structure so that the model becomes representative of the specific anatomical structure. See U.S. Pat. No. 6,295,464 which discloses a system of mapping medical images to a dynamic computer model of an anatomical structure, and using that model to derive useful parameters or to display a moving representation of the anatomy's shape and/or motion. However, such systems lack the ability to control and/or adapt operation of the imaging system based on functions or other secondary/auxiliary data related to, but not necessarily part of, the model. These systems are capable of quantifying parameters, such as measuring flow or volume, but are incapable of adapting the imaging process to optimize or otherwise augment the imaging process. Further, the disclosed quantifying or manipulation operations are performed on the model rather than on the actual anatomy.

Other known imaging systems adjust their behavior based on built in rules. For example, see U.S. Pat. Nos. 5,709,210; 6,464,640; 6,464,641; 6,423,006; 6,390,984; 6,322,509; 6,176,830; 5,800,356; 5,538,003; and 5,505,204. These systems are capable of adjusting particular imaging parameters of a given, i.e. operator set, imaging mode based on information derived from the acquired imaging data. In particular, these systems 1) process the acquired image data such that the resulting data contains detectable features corresponding to the anatomy of interest, such as by passing the data through a threshold filter to separate acoustic reflective features of a particular intensity from other features or identify areas of high flow relative to other features; 2) examine the processed data to detect the features, such as to find all features below the threshold; 3) select one of the features based on a built in rule, such as selecting the largest feature which falls below the threshold; and 4) automatically adjust particular imaging parameters based on this selection, such as by automatically placing a color pan box over the selected feature area. However, these systems perform the feature selection and control adjustments based on the operator set imaging mode, the images acquired in the operator set imaging mode and the processing of those images, rather than on the anatomical structures being imaged. This reduces the flexibility of the system and constrains the operator to having to properly select an imaging mode and obtain very specific images. By coupling the image mode selection, feature selection and control adjustments to the anatomy being imaged using an operational rule set or an anatomical model, the disclosed embodiments permit more flexibility in imaging the subject and a wider range of control adjustments which can be performed. Anatomical models further permit the disclosed embodiments to make deductions about the anatomy being imaged that are not necessarily a part of the image, i.e. they permit the system to comprehend features of the imaged anatomical structures that normally are not fully comprehensible by the system, for example by being currently at least partially outside the imaging system's field of view.

FIGS. 1A–1T depict flow charts of the operation of an imaging system, according to one embodiment, which associates an anatomical model with the imaged anatomy, or portion thereof, and applies one or more functions or other secondary/auxiliary information to effect adaptation or manipulation of the imaging system to optimize, augment or otherwise enhance the imaging process and resultant diagnosis. As will be described, signals are acquired (block 102), the signals having been derived from one or more emissions detected by a diagnostic medical imaging system from a portion of a subject, such as the thoracic portion of a human being. These signals may be electrical, optical, or compatible with another communication technology now or later developed, and further may be in an analog form or a digital representation thereof. The imaged portion contains, at least partially, at least one anatomical structure, such as the heart, heart valve, blood vessel, etc. The anatomical structure within, or at least partially within, the portion being imaged includes features that are comprehensible by the imaging system, i.e. produces emissions detectable by the imaging system. It will be appreciated that the term "emission" includes naturally occurring emissions, such as acoustic, electrical, magnetic or thermal emissions, as well as emissions caused by the induction/transmission of energy from an external source, such as x-ray, acoustic, magnetic, electrical or thermal energies, into the portion of the subject. Further, the term emission refers both to detectable energy emitted by the subject as well as the absence thereof, i.e. the detectable absorption of energy. The comprehensible features of the imaged portion may include features such as defined, actual or present structure, composition, dimensions, behavior, emission intensity, emission duration, or other features discernable from the derived signals, such as quantifiable relationships among such features.

The anatomical structure within, or at least partially within, the portion being imaged is further characterized by features which are at least partially incomprehensible by the imaging system, i.e. are not fully discernable from the detected emissions or the signals derived therefrom. Such features include dynamic/varied or expected/predicted arrangement, structure, composition, dimensions, behavior or other features of the anatomical structure not present or visible within the imaged portion. Examples of incomprehensible features include the relationship between various elements of the anatomical structure, the dynamic behavior of the anatomical structure, various ROI's within the anatomical structure, and/or characteristics of the anatomical structure which may lend themselves to more optimal imaging using a particular imaging mode or particular set of imaging parameters of the imaging system, etc.

In one embodiment, the diagnostic medical imaging systems includes a diagnostic medical ultrasound system. The emissions detected by the imaging system include ultrasonic echoes received by an ultrasound transducer coupled with the ultrasound system in response to the transmission of acoustic energy into the portion of the subject to be imaged. Herein, the phrase "coupled with" is defined to mean directly connected to or indirectly connected through one or more intermediate components. Such intermediate components may include both hardware and software based components.

In an alternate embodiment, the emissions further comprise passive emissions, such as electrical emissions related to cardiovascular activity, the derived signals representing an electrocardiogram. In this embodiment, the diagnostic medical imaging system may include an electrocardiograph device, wherein the comprehensible or at least partially incomprehensible features include electrical characteristics of the anatomical structure being imaged.

The derived signals may be acquired in real time during an imaging session or from a storage device which stores the derived signals from prior imaging sessions. Further, the derived signals may be acquired from an imaging system local to the subject being examined, or via a network from a remote imaging system.

Once the signals have been acquired, or while they are being acquired in the case of real time acquisition, the imaging system identifies the comprehensible feature(s) (block 104). As described above, this identification may be made by discerning the presence, intensity and/or duration of emissions from the subject or the lack thereof. This information may then be processed to identify features of the anatomical structures present, or at least partially present, within the imaged portion. For example, in the case of a diagnostic medical ultrasound system, acoustic reflective features may be identified within the imaged portion. In an alternative embodiment, simple rules may be applied by the imaging system to further identify features, such as emission intensity threshold functions to identify areas of high emission or void areas. Emissions of different types may be acquired and processed to enhance the identification of comprehensible features.

An anatomical model is then provided (block 106). The anatomical model may be stored on a hard disk, network or other memory coupled with the diagnostic medical imaging system. The anatomical model is essentially a model, i.e. a substantial approximation, of the anatomical structure present, or at least partially present within the imaged portion, which is comprehensible, i.e. capable of being processed, by the diagnostic medical imaging system. This model may be a volumetric or other model, a structural or behavioral model, a static or dynamic model, i.e. may model dynamic behavior of the anatomical structure, or combinations thereof. The anatomical model comprises a imaging system comprehensible model of at least one or more of the at least partially incomprehensible features of the anatomical structure, and may further model the comprehensible features as well. In particular, the anatomical model defines at least one expected characteristic of the anatomical structure, such as expected arrangement of elements of the anatomical structure, expected composition, expected dimensions, or expected emissions (presence of, intensity or duration).

In an alternate embodiment, a database comprising a plurality of anatomical models is provided, such as stored on a hard disk or network coupled with the diagnostic medical imaging system. The anatomical model which best matches the anatomical structures is then selected from this database. This selection may be based on the operational state of the diagnostic medical imaging system and, further, may be manually made by the operator or automatically determined by the diagnostic medical imaging system based on, for example, the detected comprehensible features.

In another alternative embodiment, the anatomical model database may comprise a hierarchical collection of anatomical models, wherein the collection collectively comprises a substantial approximation of an anatomical configuration comprising multiple anatomical structures. For example, a hierarchical collection of anatomical models may be provided for the heart wherein the collection includes models of the right atrium, the left atrium, the right ventricle, the left ventricle, the valves, etc. Further, each model within a given collection may itself be a collection of models of the anatomical sub-structures within the larger structure. In one embodiment, a hierarchical collection of anatomical models representing an entire human body is provided, wherein this collection includes models, or further hierarchical collections of models, representing the major organ structures, etc. It will be appreciated that the provision of anatomical models representing various anatomical structures and the division or combination of anatomical structures among or within particular anatomical models, is implementation dependent, and all such combination, divisions, and hierarchies are contemplated.

In addition, the anatomical model further includes secondary or auxiliary information. This auxiliary information is not part of the model of the anatomical structure but is associated with the model, or portions thereof, as will be described. The auxiliary information may be any information associated with the model or portions thereof. The auxiliary information may include indications of one or more ROI's within the anatomical structure, wherein the information is used by the imaging system to locate an ROI, for example, to detect fluid flow. The auxiliary information may include functions which can be executed in relation to the anatomical structure being imaged. For example, these functions may include functions which quantify attributes of the at least partially incomprehensible features of the anatomical structures such as quantifying dimensions, volume, deflection or movement of structures not completely within the field of view of the imaging system. These functions may also include functions which control the imaging system, such as functions which cause the imaging system to select a particular imaging mode or configure a particular set of imaging parameters, augment the displayed representation of the anatomical structures by, for example, highlighting particular features for the operator, or functions which manipulate, alter or otherwise adjust or enhance operation of the imaging system. For example, a function may be provided which adjusts the depth control of the transducer to optimize imaging in the case of a diagnostic medical ultrasound system. The auxiliary information may also include functions which automatically initiate modes of operation of the imaging system depending on the anatomical structure being imaged or automatically make and record particular measurements. The auxiliary information may also include rules for appending or overlapping images or rules for discerning healthy versus unhealthy anatomy, as described in more detail below. In one embodiment, the database comprises an anatomically organized database of auxiliary information, wherein the auxiliary information is stored in a data structure based on its associated anatomical structure. It will be appreciated that, as opposed to performing the above functions automatically, the imaging system may be alternatively controlled to guide, prompt or otherwise assist the operator in performing the functions manually.

Once the anatomical model has been provided, the model is associated with the imaged portion of the subject, i.e. associated with the derived signals, or portion thereof representing the anatomical structures within, or at least partially within, the imaged portion (block 108). This associating may include fitting or otherwise adjusting the model to more substantially approximate the particular anatomical structure. Such fitting may be performed based on associating the comprehensible features detected by the imaging system with the comprehensible features as modeled in the anatomical model. The resultant fitted model, being comprehensible by the imaging system as described above, may then be utilized by the imaging system to perform functions involving the at least partially incomprehensible features.

Once the anatomical model has been associated, control data is generated by the imaging system based on the association (block 110). The operation of the imaging system is then controlled as a function of the control data (block 112). As described above, this control data may be generated based on the auxiliary information contained within the anatomical model. For example, control data may be generated to alter the operation of the imaging system or otherwise augment the displayed representation of the anatomical structure being imaged. Such control/augmentations may include presenting prompts or other information to the operator to assist the operator in manual performance of particular functions as described herein.

In one embodiment wherein the imaging system comprises a diagnostic medical ultrasound system, control data may be generated to control/manipulate operation of the transducer, or guide the user in doing so, such as by altering the beam focus, beam angle, frequency or other transducer operational parameters.

Wherein the anatomical structure is characterized by an at least partially incomprehensible feature comprising dynamic or variable behavior and the anatomical model includes a model of this dynamic or variable behavior, control data may be generated based on this dynamic behavior to control the imaging system and/or prompt the user accordingly. For example, the heart is characterized by a cyclical dynamic behavior, i.e. as the heart beats, it moves in a cyclical fashion, e.g. diastole and systole. The dynamic nature of the heart's beat, e.g. the phases of the heart beat cycle, may be modeled by the anatomical model of the heart. Auxiliary information associated with this dynamic behavior may be used, once the model is associated with the actual anatomical structure, to predict the expected behavior, i.e. movement/displacement of the heart, and thereby control the imaging system to optimize the imaging process to account for the movement. For example, the focus of the transducer of a diagnostic medical ultrasound system may be dynamically adjusted synchronously with the movement of the heart such that the heart wall is always maintained in optimal focus.

In one embodiment, the diagnostic medical imaging system further displays a representation of the portion being imaged, and anatomical structures therein, based on the derived signals. The control data is then generated so as to cause the imaging system to augment the displayed representation, such as by highlighting a ROI or positioning a flow box or Doppler gate. In an alternative embodiment, the imaging system augments the displayed representation with a previously obtained representation of the same, or possibly different, portion, possibly obtained with the subject and/or imaging system in a different position and/or orientation. This allows the operator to compare and contrast images and/or create an apparent wider field of view.

In another embodiment, the diagnostic medical imaging system is capable of assembling multiple images obtained during discrete imaging sessions to create a single composite image with an apparent field of view which is larger than the system's actual field of view or to create a three dimensional image from discrete two or three dimensional images. Further, the discrete images used to create the composite image may be acquired with the subject or imaging system in any arbitrary position and/or orientation, further easing the constraints on the operator. In operation, the operator scans a subject with the subject and/or imaging system arranged in multiple positions and/or orientations, with images being acquired in each position and/or orientation. The set of emissions detected by the imaging system then comprises sub-sets of emissions associated with the discrete images acquired in each position and/or orientation. By associating the images with an anatomical model, a frame of reference is created, this frame of reference being the at least partially incomprehensible feature of the anatomical structure. The frame of reference is then used to assemble the discrete images into a composite form or otherwise normalize operation of the imaging system with respect to the varied positions and/or orientations of the subject and/or imaging system. In one embodiment, the acquired images, or a portion thereof, are displayed substantially simultaneously to user in a coordinate system common to the particular positions and/or orientations in which the images were acquired.

In another embodiment, the imaging system is capable of maintaining a fixed frame of reference even as the subject and/or imaging system are moved to different positions and/or orientations. Using the associated anatomical model, control data is generated to maintain particular system settings, such as the position of display augmentation, despite the movement of the subject and/or imaging system. For example, as the operator of a diagnostic medical ultrasound system moves the transducer, the color flow box or Doppler gate remains fixed/static on a particular area of the anatomical structure being imaged. As the field of view changes, the imaging system, using the associated anatomical model, compensates for the change in view to maintain the position of the display augmentation.

In yet another alternative embodiment, the imaging system may further determine, using the derived signals, an actual characteristic of the at least partially incomprehensible feature corresponding to the expected characteristic provided by the associated anatomical model. The control data is then generated based on the deviation between the actual and expected characteristics and the imaging system is controlled, adjusted or otherwise manipulated accordingly. The actual characteristics may include actual behavior, actual structure, actual composition, actual dimensions or actual emissions detected (presence, intensity and/or duration). In one embodiment, the imaging system is controlled so as to augment a displayed representation of the anatomical structure with information related to the computed deviation. In an alternate embodiment, the imaging system is controlled so as to compensate for the computed deviation, for example, to enhance and/or optimize the imaging process.

Figure 2:
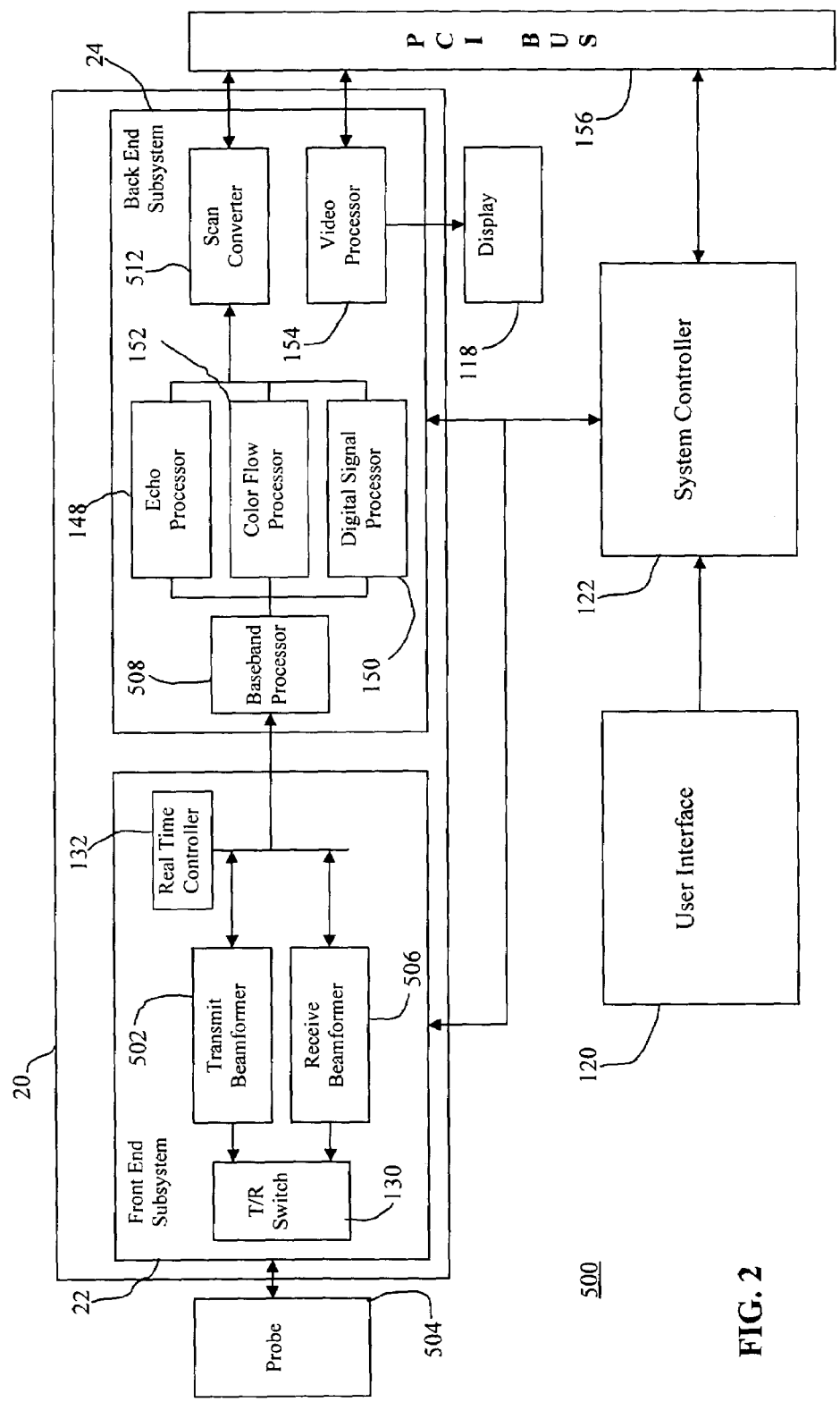
FIG. 2 depicts a block diagram of a diagnostic medical ultrasound system according to the one embodiment.

FIG. 2 shows one embodiment of a diagnostic medical ultrasound system 500. The depicted architecture corresponds to the architecture of the Sonoline Antares™ Ultrasound Platform manufactured by Siemens Medical Solutions USA, Inc., located in Iselin, N.J. It will be appreciated that one or more of the described components may be implemented in hardware, software or a combination thereof. The ultrasound system 500 includes an ultrasonic imaging probe or transducer 504, acquisition hardware 20, a front end acquisition hardware subsystem 22, a back end acquisition hardware subsystem 24, a user interface 120, a system controller 122 and a display 118. In one embodiment, the back end subsystem 24 comprises a baseband processor 508, an echo processor 148, a color flow processor 152, a digital signal processor 150, a scan converter 512 and a video processor 154. In one embodiment, the exemplary front end acquisition hardware 22 includes a transmit beamformer 502, a receive beamformer 506, a transmit/receive switch 130, and a real time controller 132. As will be discussed below, the front end acquisition hardware 22 may alternatively include local or remote optical or magnetic data storage devices such as a computer memory, hard disk, CD, DVD or video tape recorder coupled with the ultrasound system 500 via a wired or wireless device or network interface. Herein, the phrase "coupled with" is defined to mean directly connected to or indirectly connected through one or more intermediate components. Such intermediate components may include both hardware and software based components.

The front end acquisition hardware 22 is coupled with the transducer 504. The front-end acquisition hardware 22 causes the transducer 504 to generate acoustic energy into a subject and receives the electrical signals generated by the transducer 504 in response to the received echoes representing a two dimensional representation of the subject. In one embodiment, the front end acquisition hardware 22 is configurable to acquire information corresponding to a plurality of two-dimensional representations or image planes of a subject for three-dimensional reconstruction. Other configurations, such as those for acquiring data with a two dimensional, 1.5 dimensional or single element transducer array, may be used. To generate each of the plurality of two-dimensional representations of the subject during an imaging session, the acquisition hardware 20 is configured to transmit, receive and process during a plurality of transmit events. Each transmit event corresponds to firing acoustic energy along one or more ultrasound scan lines in the subject. As a result of the succession of transmit events occurring during use of the system 500, information is received continuously throughout this process.

The transmit beamformer 502 is coupled with the transducer 504 and is of a construction known in the art, such as a digital or analog based beamformer capable of generating signals at different frequencies. The transmit beamformer 502 generates one or more excitation signals which causes the transducer 504 to emit one or more ultrasonic pulses. Each excitation signal has an associated center frequency. As used herein, the center frequency represents the frequency in a band of frequencies approximately corresponding to the center of the amplitude distribution. Preferably, the center frequency of the excitation signals is within the 1 to 15 MHz range and accounts for the frequency response of the transducer 504. The excitation signals have non-zero bandwidth.

It will be appreciated that alternative methods of generating and controlling ultrasonic energy as well as receiving and interpreting echoes received therefrom for the purpose of diagnostic imaging, now or later developed, may also be used with the disclosed embodiments in addition to or in substitution of current beamforming technologies. Such technologies include technologies which use transmitters and/or receivers which eliminate the need to transmit ultrasonic energy into the subject along focused beam lines, thereby eliminating the need for a transmit beamformer, and may permit beam forming to be performed by post processing the received echoes. Such post-processing may be performed by a receive beamformer or by digital or analog signal processing techniques performed on the received echo data. For example, please refer to U.S. patent application Ser. No. 09/518,972, entitled "METHOD AND APPARATUS FOR FORMING MEDICAL ULTRASOUND IMAGES", now U.S. Pat. No. 6,309,356 and U.S. patent application Ser. No. 09/839,890, entitled "METHOD AND APPARATUS FOR FORMING MEDICAL ULTRASOUND IMAGES", the disclosures of which are herein incorporated by reference.

Control signals are provided to the transmit beamformer 502 and the receive beamformer 506 by the real time controller 132. The transducer 504, as controlled by the transmit beamformer 502, is caused to fife one or more acoustic lines in each transmit event, and the receive beamformer 506 is caused to generate in-phase and quadrature (I and Q) information along one or more scan lines. Alternatively, real value signals may be generated. A complete frame of information corresponding to a two-dimensional representation (a plurality of scan lines) is preferably acquired before information for the next frame is acquired. The real time controller 132 is also used to manage the data flow created by the receive beamformer as it collects image information, making the stream of data available to the back end subsystem 22.

Upon the firing of one or more ultrasound scan lines into the subject, some of the acoustical energy is reflected back to the transducer 504. This reflected acoustical energy is detected by the transducer 504 and converted into electrical signals which are passed to the receive beamformer 506. In addition to receiving signals at the fundamental frequency (i.e., the same frequency as that transmitted), the non-linear characteristics of tissue or optional contrast agents also produce responses at harmonic frequencies. Harmonic frequencies are frequencies associated with non-linear propagation or scattering of transmit signals. As used herein, harmonic includes subharmonics and fractional harmonics as well as second, third, fourth, and other higher harmonics. Fundamental frequencies are frequencies corresponding to linear propagation and scattering of the transmit signals of the first harmonic. Non-linear propagation or scattering corresponds to shifting energy associated with a frequency or frequencies to another frequency or frequencies. The harmonic frequency band may overlap the fundamental frequency band.

The baseband processor 508 is coupled with the receive beamformer 506 and receives the converted electrical signals representative of the reflected acoustical energy. The baseband processor 108 passes information associated with a desired frequency band, such as the fundamental band or a harmonic frequency band. In one embodiment, the baseband processor 108 may be included as part of the receive beamformer 506. Furthermore, the baseband processor 108 demodulates the summed signals to baseband. The demodulation frequency is selected in response to the fundamental center frequency or another frequency, such as a second harmonic center frequency. For example, the transmitted ultrasonic waveforms are transmitted at a 2 MHz center frequency. The summed signals are then demodulated by shifting by either the fundamental 2 MHz or the second harmonic 4 MHz center frequencies to baseband (the demodulation frequency). Other center frequencies may be used. Signals associated with frequencies other than near baseband are removed by low pass filtering. As an alternative or in addition to demodulation, the baseband processor 108 provides band pass filtering. The signals are demodulated to an intermediate frequency (IF) (e.g. 2 MHz) or not demodulated and a band pass filter is used. Thus, signals associated with frequencies other than a range of frequencies centered around the desired frequency or an intermediate frequency (IF) are filtered from the summed signals. The demodulated or filtered signal is passed to the additional processors 148, 152 and 150 as either the complex I and Q signal or other types of signals, such as real value signals. It should be noted that band pass "filtering", as well as other types of data filtering known in the art, should not be confused with the filter elements of the pipes and filters framework disclosed herein. As known in the art, "filtering" data involves allowing data with certain characteristics to pass while blocking data without those characteristics. On the other hand, while the filter elements discussed below may perform functions similar to those provided by the band pass processor 508, the filter elements, as used by the architecture described herein, are more general processing stages that manipulate, transform or enrich streaming data.

By selectively filtering which frequencies are received and processed, the backend subsystem 22 produces images with varying characteristics. In tissue harmonic imaging, no additional contrast agent is added to the target, and only the nonlinear characteristics of the tissue are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible.

Tissue harmonic images provide a particularly high spatial resolution and often possess improved contrast resolution characteristics. In particular, there is often less clutter in the near field. Additionally, because the transmit beam is generated using the fundamental frequency, the transmit beam profile is less distorted by a specific level of tissue-related phase aberration than a profile of a transmit beam formed using signals transmitted directly at the second harmonic.

The harmonic imaging technique described above can be used for both tissue and contrast agent harmonic imaging. In contrast agent harmonic imaging, any one of a number of well known nonlinear ultrasound contrast agents, such as micro-spheres or the Optison™ agent by Nycomed-Amersham of Norway, are added to the target or subject in order to enhance the non-linear response of the tissue or fluid. The contrast agents radiate ultrasonic energy at harmonics of an insonifying energy at fundamental frequencies.

The echo 148, color flow 152 and digital signal 150 processors are coupled with the baseband processor 508 and receive the filtered signals from the transducer 504/receive beamformer 506. The digital signal processor 150 comprises one or more processors for generating two-dimensional Doppler or B-mode information. For example, a B-mode image, a color Doppler velocity image (CDV), a color Doppler energy image (CDE), a Doppler Tissue image (DTI), a Color Doppler Variance image, or combinations thereof may be selected by a user. The digital signal processor 150 detects the appropriate information for the selected image. In one embodiment, the digital signal processor 150 is adapted for Doppler processing and a B-mode processing. As known in the art, the Doppler processing estimates velocity, variance of velocity and energy from the I and Q signals. As known in the art, the B-mode processing generates information representing the intensity of the echo signal associated with the I and Q signals. The echo processor 148 performs baseband and amplitude mode signal processing of RF and IQ data in a known manner. The color flow processor 152 adds color to the acquired information, as known in the art.

The information generated by the echo 148, color flow 152 and digital signal 150 processors is provided to the scan converter 512. Alternatively, the scan converter 512 includes detection processes as known in the art and described in U.S. Pat. No. 5,793,701 entitled "METHOD AND APPARATUS FOR COHERENT IMAGE FORMATION", assigned to the assignee of the present invention, the disclosure of which is herein incorporated by reference. The scan converter 512 is of a construction known in the art for arranging the output of the signal processors 148, 152 and 150 into two-dimensional representations or frames of image data. The scan converter 512 converts acoustic ultrasound line data, typically in a polar coordinate system, into data which may be plotted on a Cartesian grid. Using volume averaging or other similar algorithms on the returned echo data, the slice information is merged into a single 2D plane. This permits display of the ultrasound image on a two-dimensional output device such as a display monitor 118. Preferably, the scan converter 512 outputs formatted video image data frames, using a format such as the DICOM Medical industry image standard format or a TIFF format. Thus, the plurality of two-dimensional representations is generated. Each of the representations corresponds to a receive center frequency, such as a second harmonic center frequency, a type of imaging, such as B-mode, and positional information. It will be appreciated that the disclosed embodiments may also operate with ultrasound systems which produce three dimensional and/or four dimensional, i.e. real time 3-D, images. The harmonic based representations may have better resolution and less clutter than fundamental images. By suppressing the harmonic content of the excitation signal, the benefits of harmonic imaging of tissue may be increased. In any event, the scan converter 512 provides its output to the PCI bus 156. In one embodiment, the PCI bus 156 is a standard peripheral component interconnect board, as known.

The user interface 120 is coupled with the system controller 122 and includes one or more input devices which the clinician/sonographer/physician uses to interface with the ultrasound system 500. The user interface 120 includes input devices such as a keyboard, mouse, trackball, touch screen or other input devices or combinations thereof as are known in the art. Further the user interface 120 may also include graphic user interface ("GUI") elements coupled with the input devices and with the display 118 for both input and output functions. In addition to controlling the ultrasound functions of the ultrasound system 500, the user interface 120 may afford the user the opportunity to modify graphical representations, imaging planes and displays produced by the ultrasound system 500. Finally, the user interface 120 allows the user to coordinate multiple ultrasound probes 504.

The system controller 122 is coupled with the front end subsystem 22, the backend subsystem 22, the PCI bus 156 and the user interface 120 and controls and coordinates the functions of the ultrasound subsystems. The term "system controller" broadly refers to the appropriate hardware and/or software components of the ultrasound system 500 that can be used to implement the preferred embodiments described herein. It should be understood that any appropriate hardware (analog or digital) or software can be used and that the embodiments described herein can be implemented exclusively with hardware. Further, the system controller 122 can be separate from or combined with (in whole or in part) other processors of the ultrasound system 500 (including attendant processors), which are not shown in FIG. 2 for simplicity.

The various elements of the ultrasound system including the front end subsystem 22, backend subsystem 24 and user interface 120 are controlled in real time by the system controller 122. The system controller 122 controls the operation of the components of the system 500. A user, via the user interface 120, can adjust imaging parameters such as, but not limited to, image depth, image width, and frame rate. The controller 122 interprets the set-up information entered by the user and configures the components of the system 500 accordingly.

The video processor 154 acts as an interface between the system controller 122 and the display 118. In various embodiments, the video processor 154 can be configured to work with a variety of display types, such as cathode ray tubes or liquid crystal displays. The video processor 154 can also be configured to output information to a printer, memory, storage device, such as a computer storage device or a video recorder, computer network or other means for communicating data representative of an ultrasonic echo known in the art. The display monitor 118 is connected to the display controller 116 and is a standard display monitor as known in the art. In alternate embodiments, the display 118 can be replaced with a printer, memory, storage device, or any other output device known in the art.

Figure 3:
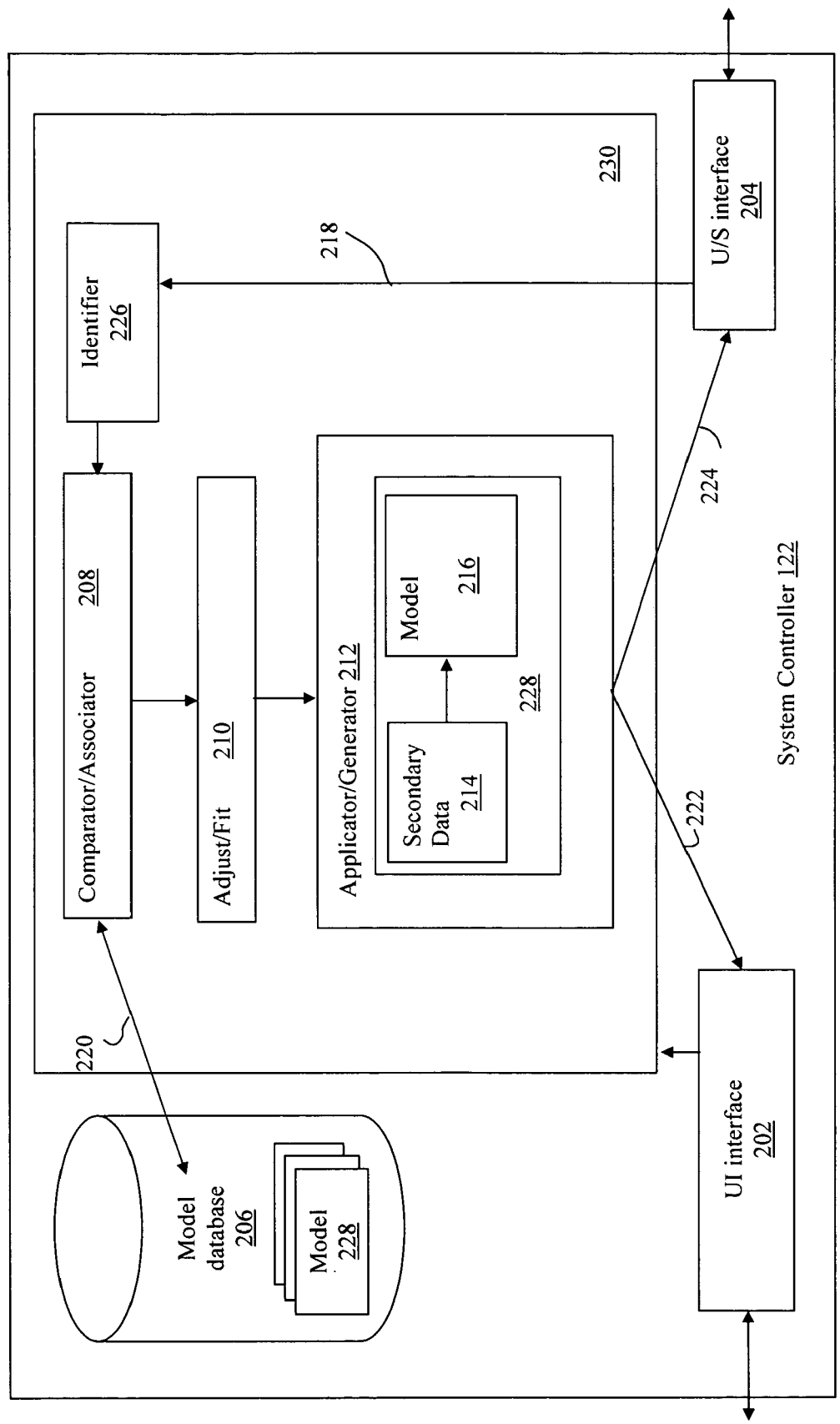
FIG. 3 depicts a block diagram of a system controller for use with diagnostic medical ultrasound system of FIG. 2.

FIG. 3 shows a block diagram of an exemplary system controller 122 for use with the diagnostic medical ultrasound system 500 described above. For clarity, some components related to the functioning of the imaging system are not shown. The system controller 122 includes a ultrasound system interface 204, a processor 230, a memory 206 and an interface to the system user interface 202. The ultrasound system interface 204 interconnects system controller 122 with the ultrasound system 500 components, as described above, so that the system controller 122 may receive digital or analog signals representing the received ultrasonic echoes as well as transmit system commands to the ultrasound system 500 components to adapt, manipulate or otherwise control the system 500. The received signals may have already been pre-processed into a digital representation thereof or may be analog, either pre-processed or received unprocessed from the transducer. In one embodiment, the interface 204 is an interface compatible with the Peripheral Component Interconnect ("PCI") Bus interface, however other bus interfaces compatible with the system bus of the ultrasound system 500 may also be used and is dependent upon the implementation. The processor 230 is coupled with the interface 204 and interprets the signals received from the ultrasound system 500, which may include converting analog signals to digital representations thereof, associates at least a subset of those signals with an anatomical model, and generates control data based on the association to control, automatic and/or via guided/prompted manual, operation of the ultrasound system 500. The processor 230 is preferably the ultrasound system 500 processor, however other processor may also be used. Further, the processing capabilities described herein may be implemented in hardware, software or a combination thereof. The memory 206 is coupled with the processor and stores the anatomical model(s) 228 for use by the processor. The memory 206 is preferably a computer storage device such as a hard disk, memory or other storage device as is known. The memory 206 may be a memory local to the ultrasound system 500 or located remotely and connected to the ultrasound system via a network. The user interface 202 includes an interface which couples the system controller 122 with the user interface of the ultrasound system 500, e.g. display or other output device, keyboard, mouse or other input device. General operation of the system controller 122 with respect to the disclosed embodiments is described above.

The processor 230 further includes identifier logic 226, association logic 208, fitting logic 210 and generator logic 212. The identifier logic 226 is coupled with the ultrasound system 500 interface 204 and receives the signals derived from the imaging process as described above. The identifier logic 226 processes the signals, or a subset thereof, to identify the comprehensible features of the anatomical structures within the imaged portion of the subject. The association logic 208 is coupled with the identifier 226 and the memory 206, described in more detail below. The association logic 208 associates the derived signals, or a subset thereof, with an anatomical model 228 stored in the memory 206. In one embodiment, the association logic 208 performs the association using the identified comprehensible features identified by the identifier logic 226. The fitting logic 210 is coupled with the association logic 208 and fits the associated anatomical model 228, if such an operation is necessary, to the corresponding actual anatomical structure present, or at least partially present, within the imaged portion of the subject. The fitting process may include scaling the dimensions of the model 228, scaling the behavior of the model 228, or otherwise altering parameters of the model 228 to match corresponding parameters of the actual anatomy. In an alternate embodiment, the fitting logic 210 determines, quantifies and/or reports deviations between one or more parameters of the anatomical model 228 and the actual anatomy. The generator logic 212 is coupled with the fitting logic 210, the interface to the system user interface 202 and the ultrasound system 500 interface 204. The generator logic 212 generates control data based on the association, and fitting if performed, of the anatomical model 228 with the derived signals. The generated control data is then used to control operation of the ultrasound system 500 and/or augment displayed representations of the imaged portions of the subject, as described above. In one embodiment, the control data is generated based on secondary/auxiliary information 214 stored with the model 228, as described above. It will be appreciated that one or more of the logic components described above may be combined or further divided into discrete sub-components.

In an alternative embodiment, position and/or orientation hardware is provided with provides accurate position and/or orientation information regarding the transducer and/or the subject or anatomy being imaged. This data is received by the system controller 122 and processed to determine the position and/or orientation of the imaging plane or volume created by the transducer and/or the position and/or orientation of the subject or anatomy being imaged relative to the imaging plane, volume or some other origin. This information can then be used to further enhance the identification and association of the anatomical model 228 as well as the generation of control data.

Figure 4B:
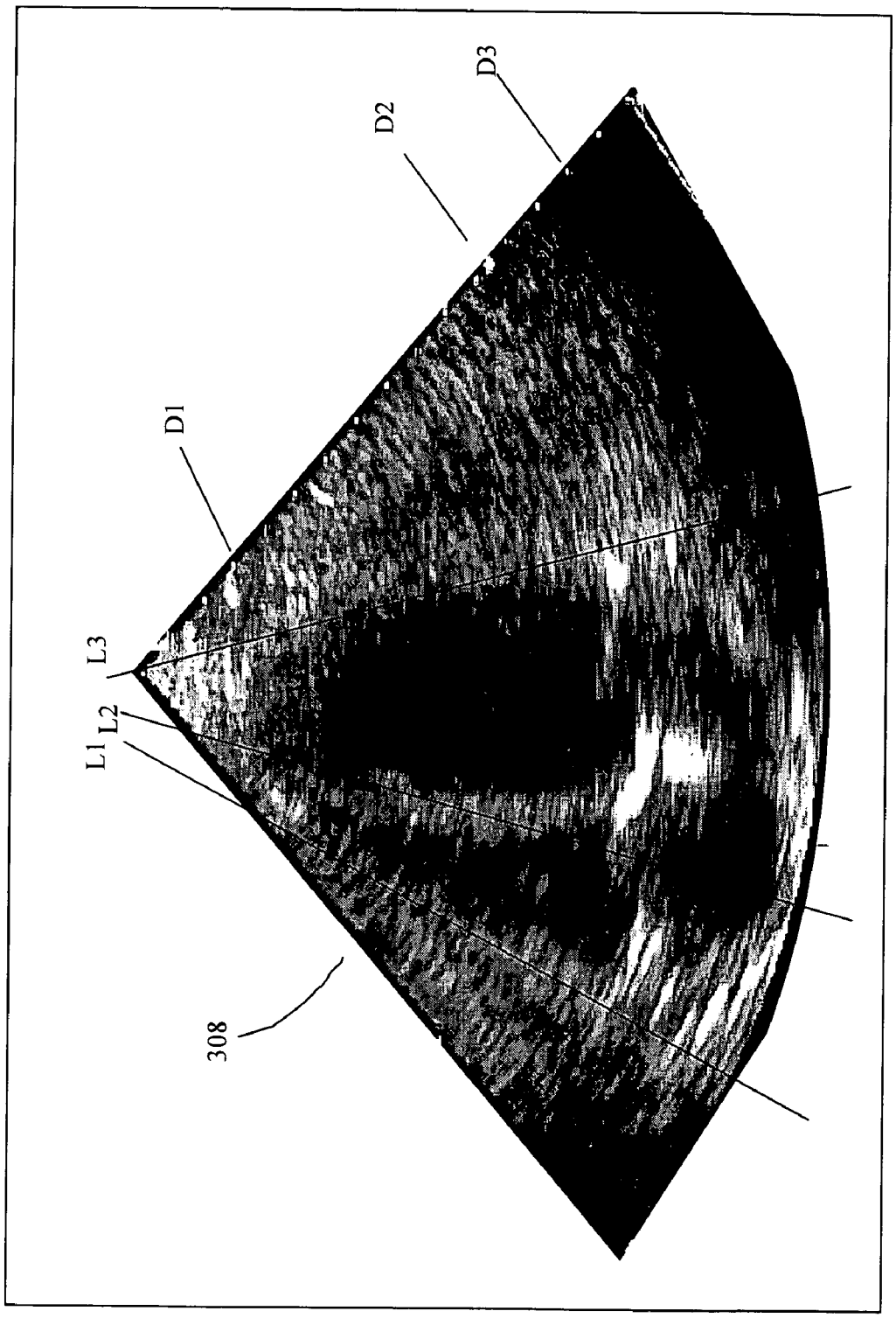
FIG. 4B depicts an exemplary ultrasound image of the heart.
Figure 4C:
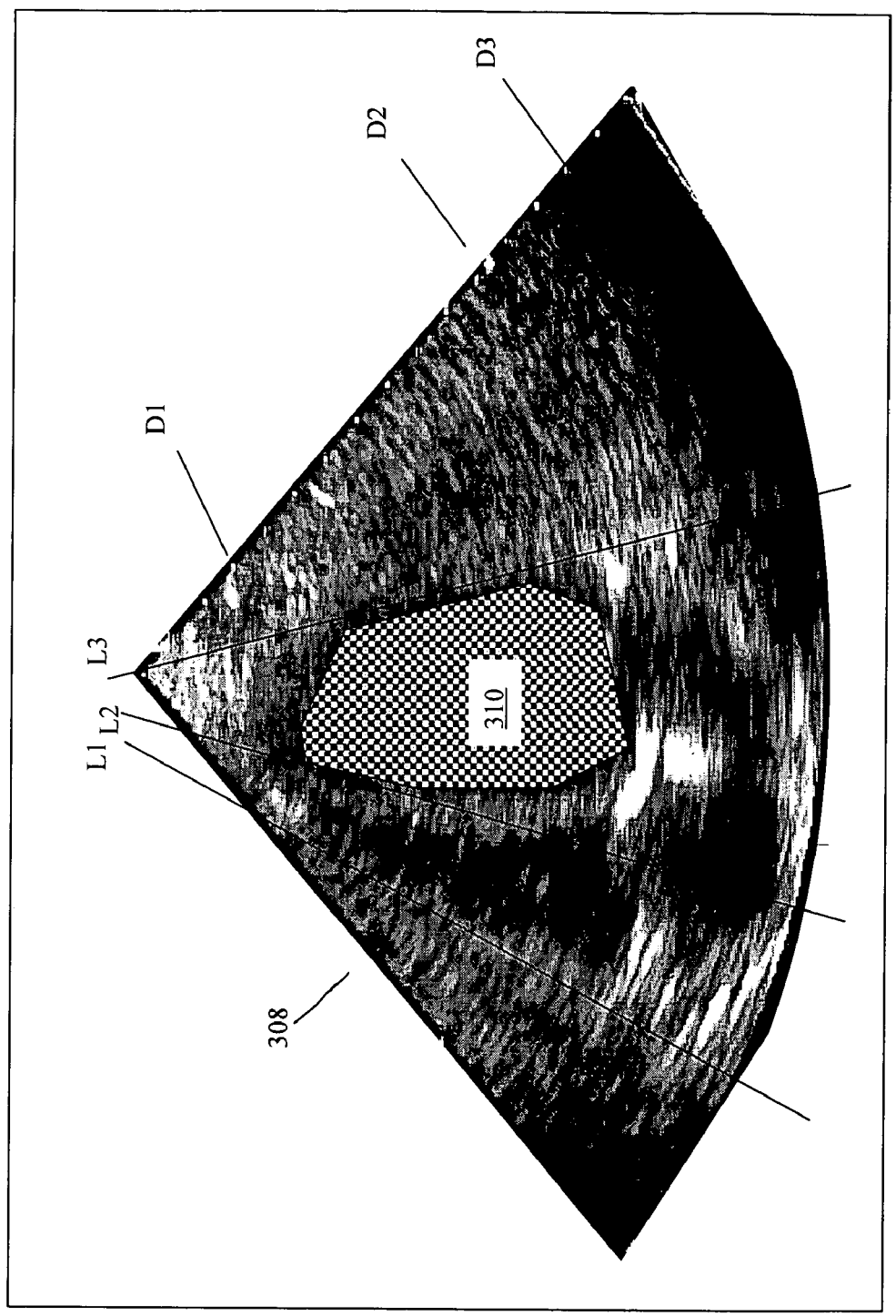
FIG. 4C depicts application of the disclosed embodiments with respect to the anatomical model of FIG. 4A and the exemplary ultrasound image of FIG. 4B.

FIGS. 4A-4C show an exemplary anatomical model as well as the process of fitting the model to the actual anatomical structure being imaged. FIG. 4A shows the anatomical model 228 for the heart. The model 228 includes a volumetric structural model 302 of the heart as well as one or more cross sectional or planar models 304 showing the internal structure of the heart as it would appear across various imaging planes. For clarity, only one exemplary imaging plane is shown. In one embodiment, the various planar models 304 may be computationally derived from the volumetric structural model 302. The model 228 further includes auxiliary information 306, which in this case, indicates regions of interest within the heart, such as the atrial and ventricular chambers of the heart. As was described above, each atrial or ventricular chamber could be represented by its own model in a hierarchical collection of models representing the overall heart structure. The auxiliary information 306 will be used by the ultrasound system 500, as described above, to augment the displayed representation of the actual heart, i.e. anatomical structure, being imaged.

FIG. 4B shows an exemplary ultrasound image of a heart. FIG. 4C shows the result of exemplary operation of the disclosed embodiments. After associating and fitting the model 228 of the heart from FIG. 4A with the image of FIG. 4B, the system 500 is able to identify and highlight 310 the left ventricular chamber using the auxiliary data 306 from the model 228.

Other exemplary applications of the disclosed embodiments include image acquisition applications, image processing applications, user interface applications and work flow applications.

An exemplary image acquisition application involves imaging a beating heart. Typically, not all parts of the heart are of equal importance for diagnosis during a given examination. Having access to auxiliary information describing the importance, orientation and/or dynamics of the portions of the heart being imaged, an imaging system 500 is capable of making tradeoffs that optimize imaging performance in imaging the diagnostically significant portions of the heart. For example, the system 500 may automatically decrease temporal resolution during diastole, thus reducing power usage and exposure of the patient to the energy emitted by the imaging system. In addition, the system 500 can automatically modulate temporal resolution throughout the field of view to better visualize fast moving structures. Further, in the case of a diagnostic medical ultrasound system, the system 500 can automatically and dynamically move the transmit focus and orientation of the ultrasonic beams to enhance visualization of a moving structure that is important for diagnosis. Additionally, acquisition parameters which are sensitive to the qualities of the anatomy being imaged that vary in a predictable fashion may be dynamically optimized. For example, the Doppler scale may be lowered during diastole to give better visualization of low flow velocities and then raised during systole to avoid aliasing.

An exemplary image processing application involves using the auxiliary information stored with each anatomical model as a container to hold processed image values, where the processing may be anything from simple copying of acquired image samples to advanced compounding involving many, or all, image samples associated with the same model element. In one embodiment, all acquired data would be stored in the model, i.e. in storage containers associated with the model elements. By pulling the displayed image out of the model, it is possible to show a field of view that encompasses everything scanned so far and not just what is being scanned at the moment. This provides an apparent extended field of view which does not require the combined images to be sequentially acquired.

An exemplary user interface application involves converting some user controls to work within an anatomical coordinate system rather than the transducer/probed coordinate system, thereby improving the usefulness and intuitiveness of the those controls. This may be accomplished by associating the control's parameters to elements of an anatomical model, and using the derived associations to determine the control's probe-relative values. For example, the system 500 may automatically position and size the Flow ROI to encompass the left ventricle when Flow is activated while imaging the left ventricle. In addition, or alternatively, the system 500 may automatically keep the spectral Doppler gate, Flow ROI, or an anatomical annotation positioned in the same location in the heart as the transducer/probe or heart moves.

An exemplary work flow application involves improving the imaging examination process. Ultrasound or other imaging system examinations typically involve a pre-defined sequence of steps, some of which can be facilitated, or even automated, by an imaging system 500 which is capable of associating the images being acquired with auxiliary information comprising rules that apply specifically to the anatomy being imaged. For example, the system 500 may automatically initiate the appropriate operating modes, using appropriately placed ROI'S, as the operator progresses through the exam. Further, the system 500 may automatically make and record certain anatomic measurements, such as fetal bone lengths.

Additionally, a repository of anatomically organized rules may be provided which include expert operator tips or tricks to obtain optimal images in specific situations. For example, an anatomical model of the liver may be provided with the capability to model cysts possibly present in a diseased liver. Whenever a portion of an acquired image is associated with the model of the cyst, the imaging system 500 may automatically transmit a sequence of energies designed to induce flow within any fluid inside the cyst, and then initiate an operational mode which detects and/or measures that flow, using an ROI centered on the cyst. This would allow the operator to distinguish between solid and fluid-filled cysts without having to manually execute a complicated series of operations.

In another embodiment of the exemplary diagnostic medical imaging system above, the system is capable of identifying one or more comprehensible, or at least partially comprehensible, features of the anatomical structures present, or at least partially present, within the imaged portion based on the emissions received by the transducer. The identification may be performed utilizing an anatomical model, as describe above, and/or using operational rules, such as intensity thresholds, etc, as described above.

In one embodiment, once a feature is identified, the imaging system is further capable of automatically initiating, i.e. activating or prompting the operator to activate, an imaging mode of the diagnostic medical imaging system to optimally image the identified feature, in addition to optimizing the imaging parameters of an automatically, or manually, selected imaging mode. An imaging mode is defined as a method of acquiring and processing ultrasound information and includes particular pre-processing of transducer control signals to control the characteristics of the generated acoustic energy, particular post-processing of received echoes as well as the method and format of rendering the displayed representation of those post-processed echoes. Imaging modes include combinations of transducer settings, echo processing techniques, visual rendering processing and/or GUI augmentation. An imaging mode may be characterized by one or more parameters which may adjusted, either automatically or manually, to optimize or enhance the imaging mode. Such parameters may include harmonic imaging parameters. Further, imaging modes may be used with or without contrast agents.

Exemplary imaging modes include time based and frame based imaging modes. Time based imaging modes include M-mode, PW-mode, CW-mode, and Color M-mode. Time based imaging modes provide enhanced visualization of change over time of an imaged feature and are typically displayed so as to show relationship to time.

M-mode (Motion-mode) displays ultrasonic echo strength as a function of depth over time. Typically, the display renders a two dimensional image, wherein the vertical axis represents depth and horizontal axis represents time. The displayed value represents the strength of the ultrasonic echo from a point at the given depth, along a line into the portion of the subject being imaged. This mode is useful for visualizing tissue motion along the depth dimension as a function of time.

PW-mode (Pulsed-wave Doppler) is used to detect and display the velocity of movement within the imaged portion, and typically within a specific ROI of the imaged portion. Typically, the display renders a two dimensional image, wherein the vertical axis represents velocity and the horizontal axis represents time. The displayed value represents the amount of material within a specified ROI that is moving at the given velocity. This mode is useful for visualizing variation in the velocity spectrum of blood over time.

CW-mode (Continuous-wave Doppler) is similar to PW-mode, except that the ROI is not restricted in range, and the velocity spectrum is cleaner as a result.

Color M-mode is similar to M-mode wherein the displayed vertical axis represents depth. However, the value displayed represents average velocity, energy, variance, or a combination thereof, at the given depth, along a line into the portion of the subject being imaged.

Frame based imaging modes include B-mode and F-mode. Frame-based imaging modes provide enhanced visualization spatial or dimensional change. Frame based imaging modes render and display images using spatial dimensions as the axes.

B-mode (Brightness mode) is similar to M-mode and displays values representing the strength of the ultrasound echo from a specific location, usually displayed by varying the brightness/intensity level of the displayed pixels which corresponds to the echo strength. This imaging mode is useful for visualizing the structure and arrangement of tissue.

F-mode (also referred to as Color Doppler or Color Flow) is similar to Color M-mode and displays values representing an average velocity (or energy, etc) from a specific location. This imaging mode is useful for visualizing blood flow.

It will be appreciated that there may be other imaging modes, both Time and Frame based, and that one of more imaging modes may be combined or simultaneously displayed.

In another embodiment, once a feature is identified, the imaging system configures a set of operating parameters to control operation of said diagnostic medical ultrasound system based on the identified feature. Diagnostic medical ultrasound imaging systems often feature multiple configurable settings to control the system and optimize and/or enhance the imaging and/or diagnostic process. Various settings may be related while other settings are separate/distinct from each other. In this embodiment, collections or groups of settings, whether disparate or related, may be collectively configured automatically by the system based on the identified feature being imaged. The system may include numerous, potentially overlapping, configuration sets, each set specifying ideal settings of various parameters of the system. These configuration sets may be stored in a memory within the system or on a network. By automatically identifying the feature(s) being imaged and configuring the multitude of imaging parameters necessary to optimally image the feature(s) and perform the diagnosis, operation of the imaging system is greatly simplified. The various configuration sets may be further categorized by the type of examination to be performed on the identified feature, wherein the different examinations of any one identified feature may be optimized by particular system settings. Once the feature being imaged is identified, the user may be prompted to select an exam type, the selection of which causes automatic configuration of the multitude of operating/imaging parameters to optimize and/or enhance the examination process.

In yet another embodiment, once a feature is identified, the imaging system may automatically guide the operator through a plurality of examination procedures based on said identified feature. Many diagnostic procedures follow a protocol of examination stages, each of which may require configuring the imaging system in a different manner to obtain the requisite diagnostic information. In this embodiment, once the imaged feature is identified, the imaging system automatically determines an examination protocol and guides/prompts the operator through performing each of the particular stages. In guiding and/or prompting the operator, the imaging system may automatically configure itself, as described above, or prompt the user to manually configure the system.

It is therefore intended that the foregoing detailed description be regarded as illustrative rather than limiting, and that it be understood that it is the following claims, including all equivalents, that are intended to define the spirit and scope of this invention.

We claim:

1. A method for controlling the operation of a diagnostic medical imaging system, said method comprising:
receiving a plurality of signals, each of said plurality of signals having been derived from an emission detected by said diagnostic medical imaging system from a portion of a subject, said portion characterized by a first feature comprehensible by said diagnostic medical imaging system from at least one of said plurality of signals and a second feature at least partially incomprehensible by said diagnostic medical imaging system from said plurality of signals, said first and second features comprising first and second features of at least one anatomical structure at least partially present in said portion;
identifying said first feature by said diagnostic medical imaging system;
providing an anatomical model, said anatomical model comprising a substantial approximation of said second feature of said at least one anatomical structure, said anatomical model being comprehensible by said diagnostic medical imaging system and defining at least one expected characteristic of said second feature;
associating a subset of said plurality of signals with said anatomical model based on said first feature;
generating control data based on said associating; and
controlling receiving of a subsequent plurality of signals by said diagnostic medical imaging system as a function of said control data.

2. The method of claim 1, wherein said first feature is characterized by at least one of a defined behavior, a defined structure, a defined composition, at least one defined dimension, and a defined emission.

3. The method of claim 1, wherein said second feature is characterized by at least one of a varied arrangement, a varied behavior, a varied structure, a varied composition, at least one varied dimension, and a varied emission.

4. The method of claim 1, wherein said at least one expected characteristic comprises at least one of expected arrangement, expected behavior, expected structure, expected composition, at least one expected dimension, and expected emission.

5. The method of claim 1, further comprising:
selecting said anatomical model from a database comprising a plurality of said anatomical models.

6. The method of claim 5, wherein said selecting further comprises automatically selecting said anatomical model based on said first feature.

7. The method of claim 5, wherein said selecting further comprises selecting said anatomical model based on an operational state of said diagnostic medical imaging system.

8. The method of claim 5, wherein said plurality of said anatomical models collectively comprise a substantial approximation of an anatomical configuration encompassing said at least one anatomical structure.

9. The method of claim 5, wherein said anatomical model further comprises at least one function capable of being performed by said diagnostic medical imaging system in relation to said second feature, said processor being further operative to apply said at least one function to alter an operational state of said diagnostic medical imaging system based on said anatomical model, said database comprising an anatomically organized database of each of said at least one function, each of said at least one function being stored in a data structure based on its associated anatomical structure.

10. The method of claim 1, wherein said anatomical structure is characterized by a dynamic behavior, said second feature comprising said dynamic behavior.

11. The method of claim 1, wherein said associating further comprises adjusting said anatomical model to substantially approximate said anatomical structure.

12. The method of claim 1, wherein said anatomical model further comprises at least one function capable of being performed by said diagnostic medical imaging system in relation to said second feature, said generating further comprising applying said at least one function to alter an operational state of said diagnostic medical imaging system based on said anatomical model.

13. The method of claim 1, further comprising:
determining at least one actual characteristic of said second feature corresponding with said at least one expected characteristic utilizing said associated subset of said plurality of signals;
wherein said controlling further comprises adjusting said diagnostic medical imaging system based on a deviation between said at least one actual characteristic and said at least one expected characteristic.

14. The method of claim 13, wherein said adjusting further comprises adjusting said diagnostic medical imaging system to compensate for said deviation.

15. The method of claim 1, wherein said diagnostic medical imaging system comprises a diagnostic medical ultrasound system.

16. The method of claim 15, wherein said emission comprises an ultrasonic echo received by an ultrasound transducer from said subject in response to transmission of acoustic energy into said portion of said subject by said transducer.

17. The method of claim 16, wherein said controlling further comprises manipulating operation of said transducer.

18. The method of claim 1, wherein said plurality of signals comprise an electrocardiogram.

19. The method of claim 1, wherein said emission is emitted in response to transmission of energy into said portion of said subject by said diagnostic medical imaging system.

20. The method of claim 1, further comprising:
displaying a representation of said plurality of signals on a display coupled with said diagnostic medical imaging system;
augmenting said representation based on said control data.

21. The method of claim 1, wherein said second feature comprises a variable behavior, said controlling further comprising dynamically controlling said operation of said diagnostic medical imaging system based on said variable behavior.

22. The method of claim 1, wherein said emission further comprises a first sub-emission and a second sub-emission, said first sub-emission being detected by said diagnostic medical imaging system when said subject is in a first orientation and position relative to said diagnostic medical imaging system and said second sub-emission being detected by said diagnostic medical imaging system when said subject is in a second orientation and position relative to said diagnostic medical imaging system, said second orientation and position being different from said first orientation and position, said generating further comprising generating said control data so as to normalize operation of said diagnostic medical imaging system with respect to a first sub-set of said plurality of signals corresponding to said first sub-emission with operation of said diagnostic medical imaging system with respect to a second sub-set of said plurality of signals corresponding to said second sub-emission.

23. The method of claim 22, wherein said controlling further comprises substantially simultaneously displaying a representation of said first and second sub-emission in a coordinate system common to both said first and second positions and orientations.

24. A diagnostic medical imaging system comprising:
a receiver operative to receive a plurality of signals, each of said plurality of signals having been derived from an emission detected by said diagnostic medical imaging system from a portion of a subject, said portion characterized by a first feature comprehensible by said diagnostic medical imaging system from at least one of said plurality of signals and a second feature at least partially incomprehensible by said diagnostic medical imaging system from said plurality of signals, said first and second features comprising first and second features of at least one anatomical structure at least partially present in said portion;
a processor coupled with said receiver and operative to receive said plurality of signals from said receiver and to identify said first feature;
a memory coupled with said processor and operative to store an anatomical model, said anatomical model comprising a substantial approximation of said second feature of said at least one anatomical structure, said anatomical model being comprehensible by said diagnostic medical imaging system and defining at least one expected characteristic of said second feature;
wherein said processor is further operative to associate a subset of said plurality of signals with said anatomical model based on said first feature, generate control data based on said association, and control operation or said receiver to receive a subsequent plurality of signals as a function of said control data.

25. The diagnostic medical imaging system of claim 24, wherein said first feature is characterized by at least one of a defined behavior, a defined structure, a defined composition, at least one defined dimension, and a defined emission.

26. The diagnostic medical imaging system of claim 24, wherein said second feature is characterized by at least one of a variable arrangement, a varied behavior, a varied structure, a varied composition, at least one varied dimension, and a varied emission.

27. The diagnostic medical imaging system of claim 24, wherein said at least one expected characteristic comprises at least one of expected arrangement, expected behavior, expected structure, expected composition, at least one expected dimension, and expected emission.

28. The diagnostic medical imaging system of claim 24, wherein said memory is further operative to store a database comprising a plurality of anatomical models, said processor being further operative to select said anatomical model from said database.

29. The diagnostic medical imaging system of claim 28, wherein said processor is further operative to automatically select said anatomical model based on said first feature.

30. The diagnostic medical imaging system of claim 28, wherein said processor is further operative to select said anatomical model based on an operational state of said diagnostic medical imaging system.

31. The diagnostic medical imaging system of claim 28, wherein said plurality of said anatomical models collectively comprise a substantial approximation of an anatomical configuration encompassing said at least one anatomical structure.

32. The diagnostic medical imaging system of claim 28, wherein said anatomical model further comprises at least one function capable of being performed by said diagnostic medical imaging system m relation to said second feature, said processor being further operative to apply said at least one function to alter an operational state of said diagnostic medical imaging system based on said anatomical model, said database comprising an anatomically organized database of each of said at least one function, each of said at least one function being stored in a data structure based on its associated anatomical structure.

33. The diagnostic medical imaging system of claim 24, wherein said anatomical structure is characterized by a dynamic behavior, said second feature comprising said dynamic behavior.

34. The diagnostic medical imaging system of claim 24, wherein said processor is further operative to adjust said anatomical model to substantially approximate said anatomical structure.

35. The diagnostic medical imaging system of claim 24, wherein said anatomical model further comprises at least one function capable of being performed by said diagnostic medical imaging system in relation to said second feature, said processor being further operative to apply said at least one function to alter an operational state of said diagnostic medical imaging system based on said anatomical model.

36. The diagnostic medical imaging system of claim 24, wherein said processor is further operative to determine at least one actual characteristic of said second feature corresponding with said at least one expected characteristic utilizing said associated subset of said plurality of signals and generate said control data to adjust said diagnostic medical imaging system based an a deviation between said at least one actual characteristic and said at least one expected characteristic.

37. The diagnostic medical imaging system of claim 36, wherein said processor is further operative to generate said control data to adjust said diagnostic medical imaging system to compensate for said deviation.

38. The diagnostic medical imaging system of claim 24, wherein said diagnostic medical imaging system comprises a diagnostic medical ultrasound system.

39. The diagnostic medical imaging system of claim 38, wherein said emission comprises an ultrasonic echo received by an ultrasound transducer from said subject in response to transmission of acoustic energy into said portion of said subject by said transducer.

40. The diagnostic medical imaging system of claim 39, wherein said processor is further operative to manipulate operation of said transducer.

41. The diagnostic medical imaging system of claim 24, wherein said plurality of signals comprise an electrocardiogram.

42. The diagnostic medical imaging system of claim 24, wherein said emission is emitted in response to transmission of energy into said portion of said subject by said diagnostic medical imaging system.

43. The diagnostic medical imaging system or claim 24, further comprising a display coupled with said processor and operative to display a representation of said plurality of signals on a display coupled with said diagnostic medical imaging system, and wherein said processor is further operative to augment said representation based on said control data.

44. The diagnostic medical imaging system of claim 24, wherein said second feature comprises a variable behavior, said processor being operative to dynamically control said operation of said diagnostic medical imaging system based on said variable behavior.

45. The diagnostic medical imaging system of claim 24, wherein said emission further comprises a first sub-emission and a second sub-emission, said first sub-emission being detected by said diagnostic medical imaging system when said subject is in a first orientation and position relative to said diagnostic medical imaging system and said second sub-emission being detected by said diagnostic medical imaging system when said subject is in a second orientation and position relative to said diagnostic medical imaging system, said second orientation and position being different from said first orientation and position, said processor being further operative to generate said control data so as to normalize operation of said diagnostic medical imaging system with respect to a first sub-set of said plurality of signals corresponding to said first sub-emission with operation of said diagnostic medical imaging system with respect to a second sub-set of said plurality of signals corresponding to said second sub-emission.

46. The diagnostic medical imaging system of claim 45, wherein said processor is further operative to substantially simultaneously generate a display of a representation of said first and second sub-emission in a coordinate system common to both said first and second positions and orientations.

47. A diagnostic medical imaging system comprising:
receiving means for receiving a plurality of signals, each of said plurality of signals having been derived from an emission detected by said diagnostic medical imaging system from a portion of a subject, said portion characterized by a first feature comprehensible by said diagnostic medical imaging system from at least one of said plurality of signals and a second feature at least partially incomprehensible by said diagnostic medical imaging system from said plurality of signals, said first and second features comprising first and second features of at least one anatomical structure at least partially present in said portion;
identifying means for identifying said first feature by said diagnostic medical imaging system;
model means for providing an anatomical model, said anatomical model comprising a substantial approximation of said second feature of said at least one anatomical structure, said anatomical model being comprehensible by said diagnostic medical imaging system and defining at least one expected characteristic of said second feature;
processing means for associating a subset of said plurality of signals with said anatomical model based on said first feature, generating control data based on said associating, and controlling said receiving means as a function of said control data to receive a subsequent plurality of signals.

48. A method for controlling operation of a diagnostic medical ultrasound system, said method comprising:
receiving a plurality of signals, each of said plurality of signals having been derived from an ultrasonic echo received by an ultrasound transducer from a portion of a subject in response to transmission of acoustic energy into said portion by said transducer;
identifying a feature of at least one anatomical structure at least partially present within said portion based on at least one of said plurality of signals;
initiating, automatically, an imaging mode of said diagnostic medical ultrasound system to control receiving of a subsequent plurality of signals based on said identified feature.

49. A method for controlling operation of a diagnostic medical ultrasound system, said method comprising:
receiving a plurality of signals, each of said plurality of signals having been derived from an ultrasonic echo received by an ultrasound transducer from a portion of a subject in response to transmission of acoustic energy into said portion by said transducer, identifying a feature of at least one anatomical structure at least partially present within said portion based on at least one of said plurality of signals;

configuring, automatically, a set of operating parameters to control receiving of a subsequent plurality of signals by said diagnostic medical ultrasound system based on said identified feature.

50. A method for controlling operation of a diagnostic medical ultrasound system, said method comprising:

receiving a plurality of signals, each of said plurality of signals having been derived from an ultrasonic echo received by an ultrasound transducer from a portion of a subject in response to transmission of acoustic energy into said portion by said transducer;

identifying a feature of at least one anatomical structure at least partially present within said portion based on at least one of said plurality of signals;

guiding, automatically, an operator of said diagnostic medical ultrasound system through a plurality of examination procedures based on said identified feature, the operator being guided as to how to control the receiving of a subsequent plurality of signals by the diagnostic medical ultrasound system.

* * * * *